US012678278B2

(12) United States Patent
Abunassar et al.

(10) Patent No.: US 12,678,278 B2
(45) Date of Patent: Jul. 14, 2026

(54) TUNABLE FIXATION DEVICE

(71) Applicant: Evalve, Inc., Santa Clara, CA (US)

(72) Inventors: Chad J. Abunassar, Alameda, CA (US); Grant Glaze, San Francisco, CA (US); Cindy Chaoyun Yang, San Francisco, CA (US); Jill Mccoy, Los Altos, CA (US); Jessie A. Garcia, Newark, CA (US); Jonathan Cox, Saratoga, CA (US); Samir Jain, Mountain View, CA (US); Scott Mosher, San Francisco, CA (US); Roisin Verbael, Redwood City, CA (US)

(73) Assignee: Evalve, Inc., Santa Clara, CA (US)

( * ) Notice: Subject to any disclaimer, the term of this patent is extended or adjusted under 35 U.S.C. 154(b) by 432 days.

(21) Appl. No.: 18/512,143

(22) Filed: Nov. 17, 2023

(65) Prior Publication Data

US 2024/0164896 A1     May 23, 2024

Related U.S. Application Data

(60) Provisional application No. 63/384,343, filed on Nov. 18, 2022.

(51) Int. Cl.
A61F 2/24 (2006.01)
(52) U.S. Cl.
CPC .......... A61F 2/2418 (2013.01); A61F 2/2427 (2013.01); A61F 2220/0075 (2013.01)

(58) Field of Classification Search
CPC .......... A61F 2/24; A61F 2/246; A61F 2/2418; A61F 2/2427; A61F 2/2466;
(Continued)

(56) References Cited

U.S. PATENT DOCUMENTS

| | | |
|---|---|---|
| 3,378,010 A | 4/1968 | Codling |
| 3,874,388 A | 4/1975 | King |

(Continued)

FOREIGN PATENT DOCUMENTS

| | | |
|---|---|---|
| CA | 2296317 C | 1/2009 |
| CN | 106102599 | 11/2016 |

(Continued)

*Primary Examiner* — Vi X Nguyen
(74) *Attorney, Agent, or Firm* — SLEMAN & LUND LLP

(57) ABSTRACT

A tunable fixation device for fixation of heart valve leaflets includes a central assembly, an arm moveably coupled to the central assembly, and a gripping element moveable relative to the arm to capture a native leaflet therebetween. The arm has a body portion and a wire frame coupled to the body portion. The wire frame has a first and second wire segment, and an interconnection portion interconnecting the first and second wire segments. The interconnection portion is slidingly engaged with the body portion. The first wire segment is configured to deform upon force applied to the second wire segment by sliding movement of the interconnection portion relative to the body portion, and the second wire segment is configured to deform upon force applied to the first wire segment by sliding movement of the interconnection portion relative to the body portion.

20 Claims, 17 Drawing Sheets

(58) Field of Classification Search
CPC . A61F 2220/0075; A61B 17/00; A61B 17/08;
A61B 17/00234; A61B 17/0401
See application file for complete search history.

(56) References Cited

U.S. PATENT DOCUMENTS

| | | | |
|---|---|---|---|
| 4,007,743 A | 2/1977 | Blake |
| 4,055,861 A | 11/1977 | Carpentier |
| 4,327,736 A | 5/1982 | Inoue |
| 4,340,091 A | 7/1982 | Skelton |
| 4,657,024 A | 4/1987 | Coneys |
| 4,693,248 A | 9/1987 | Failla |
| 4,716,886 A | 1/1988 | Schulman |
| 4,795,458 A | 1/1989 | Regan |
| 4,809,695 A | 3/1989 | Gwathmey |
| 4,930,674 A | 6/1990 | Barak |
| 5,002,562 A | 3/1991 | Oberlander |
| 5,069,679 A | 12/1991 | Taheri |
| 5,098,440 A | 3/1992 | Hillstead |
| 5,125,895 A | 6/1992 | Buchbinder |
| 5,147,370 A | 9/1992 | McNamara |
| 5,171,259 A | 12/1992 | Inoue |
| 5,222,963 A | 6/1993 | Brinkerhoff |
| 5,271,544 A | 12/1993 | Fox |
| 5,327,905 A | 7/1994 | Avitall |
| 5,330,501 A | 7/1994 | Tovey |
| 5,334,217 A | 8/1994 | Das |
| 5,363,861 A | 11/1994 | Edwards |
| 5,389,077 A | 2/1995 | Melinyshyn |
| 5,403,326 A | 4/1995 | Harrison |
| 5,425,744 A | 6/1995 | Fagan |
| 5,450,860 A | 9/1995 | O'Connor |
| 5,452,837 A | 9/1995 | Williamson, IV |
| 5,456,400 A | 10/1995 | Shichman |
| 5,456,674 A | 10/1995 | Bos |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop |
| 5,601,574 A | 2/1997 | Stefanchik |
| 5,607,462 A | 3/1997 | Imran |
| 5,607,471 A | 3/1997 | Seguin |
| 5,609,598 A | 3/1997 | Laufer |
| 5,611,794 A | 3/1997 | Sauer |
| 5,636,634 A | 6/1997 | Kordis |
| 5,695,504 A | 12/1997 | Gifford, III |
| 5,713,911 A | 2/1998 | Racenet |
| 5,716,417 A | 2/1998 | Girard |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens |
| 5,810,847 A | 9/1998 | Laufer |
| 5,814,097 A | 9/1998 | Sterman |
| 5,843,178 A | 12/1998 | Vanney |
| 5,849,019 A | 12/1998 | Yoon |
| 5,855,601 A | 1/1999 | Bessler |
| 5,976,159 A | 11/1999 | Bolduc |
| 6,015,417 A | 1/2000 | Reynolds, Jr. |
| 6,048,351 A | 4/2000 | Gordon |
| 6,079,414 A | 6/2000 | Roth |
| 6,117,144 A | 9/2000 | Nobles |
| 6,120,496 A | 9/2000 | Whayne |
| 6,149,658 A | 11/2000 | Gardiner |
| 6,165,183 A | 12/2000 | Kuehn |
| 6,182,664 B1 | 2/2001 | Cosgrove |
| 6,193,734 B1 | 2/2001 | Bolduc |
| 6,200,315 B1 | 3/2001 | Gaiser |
| 6,217,528 B1 | 4/2001 | Koblish |
| 6,269,819 B1 | 8/2001 | Oz |
| 6,290,674 B1 | 9/2001 | Roue |
| 6,312,447 B1 | 11/2001 | Grimes |
| 6,332,880 B1 | 12/2001 | Yang |
| 6,346,074 B1 | 2/2002 | Roth |
| 6,419,696 B1 | 7/2002 | Ortiz |

| | | | |
|---|---|---|---|
| 6,461,366 B1 | 10/2002 | Seguin |
| 6,482,224 B1 | 11/2002 | Michler |
| 6,496,420 B2 | 12/2002 | Manning |
| 6,544,215 B1 | 4/2003 | Bencini |
| 6,551,303 B1 | 4/2003 | Van Tassel |
| 6,575,971 B2 | 6/2003 | Hauck |
| 6,599,311 B1 | 7/2003 | Biggs |
| 6,626,930 B1 | 9/2003 | Allen |
| 6,629,534 B1 | 10/2003 | Frederick |
| 6,669,687 B1 | 12/2003 | Saadat |
| 6,695,866 B1 | 2/2004 | Kuehn |
| 6,719,767 B1 | 4/2004 | Kimblad |
| 6,752,813 B2 | 6/2004 | Goldfarb |
| 6,770,083 B2 | 8/2004 | Seguin |
| 6,797,002 B2 | 9/2004 | Spence |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen |
| 7,011,669 B2 | 3/2006 | Kimblad |
| 7,101,395 B2 | 9/2006 | Tremulis |
| 7,112,207 B2 | 9/2006 | Allen |
| 7,125,421 B2 | 10/2006 | Tremulis |
| 7,226,467 B2 | 6/2007 | Lucatero |
| 7,556,632 B2 | 7/2009 | Zadno |
| 7,563,267 B2 | 7/2009 | Goldfarb |
| 7,569,062 B1 | 8/2009 | Kuehn |
| 7,604,646 B2 | 10/2009 | Goldfarb |
| 7,635,329 B2 | 12/2009 | Goldfarb |
| 7,655,015 B2 | 2/2010 | Goldfarb |
| 7,666,204 B2 | 2/2010 | Thornton |
| 7,736,388 B2 | 6/2010 | Goldfarb |
| 7,811,296 B2 | 10/2010 | Goldfarb |
| 7,972,323 B1 | 7/2011 | Bencini |
| 7,981,139 B2 | 7/2011 | Martin |
| 8,057,493 B2 | 11/2011 | Goldfarb |
| 8,062,313 B2 | 11/2011 | Kimblad |
| 8,118,822 B2 | 2/2012 | Schaller |
| 8,216,230 B2 | 7/2012 | Hauck |
| 8,216,256 B2 | 7/2012 | Raschdorf, Jr. |
| 8,303,608 B2 | 11/2012 | Goldfarb |
| 8,500,761 B2 | 8/2013 | Goldfarb |
| 8,734,505 B2 | 5/2014 | Goldfarb |
| 8,740,920 B2 * | 6/2014 | Goldfarb ............ A61B 17/0644 |
| | | 606/151 |
| 9,510,829 B2 | 12/2016 | Goldfarb |
| 10,076,415 B1 | 9/2018 | Metchik |
| 10,105,222 B1 | 10/2018 | Metchik |
| 10,123,873 B1 | 11/2018 | Metchik |
| 10,130,475 B1 | 11/2018 | Metchik |
| 10,136,993 B1 | 11/2018 | Metchik |
| 10,159,570 B1 | 12/2018 | Metchik |
| 10,231,837 B1 | 3/2019 | Metchik |
| 10,238,493 B1 | 3/2019 | Metchik |
| 10,245,144 B1 | 4/2019 | Metchik |
| D847,983 S | 5/2019 | Ho |
| 10,314,586 B2 | 6/2019 | Greenberg |
| 10,413,408 B2 | 9/2019 | Krone |
| 10,507,109 B2 | 12/2019 | Metchik |
| 10,517,726 B2 | 12/2019 | Chau |
| 10,524,792 B2 | 1/2020 | Hernandez |
| 10,595,997 B2 | 3/2020 | Metchik |
| 10,646,342 B1 | 5/2020 | Marr |
| 10,779,837 B2 | 9/2020 | Lee |
| D902,403 S | 11/2020 | Marsot |
| 10,856,988 B2 | 12/2020 | Mcniven |
| 11,464,636 B2 | 10/2022 | Abunassar |
| 11,660,189 B2 | 5/2023 | Abunassar |
| 2002/0013571 A1 | 1/2002 | Goldfarb |
| 2002/0183787 A1 | 12/2002 | Wahr |
| 2003/0069593 A1 | 4/2003 | Tremulis |
| 2003/0167071 A1 | 9/2003 | Martin |
| 2004/0034365 A1 | 2/2004 | Lentz |
| 2004/0044350 A1 | 3/2004 | Martin |
| 2005/0267493 A1 | 12/2005 | Schreck |
| 2006/0020275 A1 | 1/2006 | Goldfarb |
| 2006/0089671 A1 | 4/2006 | Goldfarb |
| 2007/0038293 A1 | 2/2007 | St. Goar |

(56)                    References Cited

U.S. PATENT DOCUMENTS

| | | | |
|---|---|---|---|
| 2011/0004227 A1 | 1/2011 | Goldfarb | |
| 2011/0251683 A1* | 10/2011 | Tabor | A61F 2/2436 623/2.11 |
| 2017/0042546 A1* | 2/2017 | Goldfarb | A61M 25/0147 |
| 2017/0049455 A1 | 2/2017 | Seguin | |
| 2017/0239048 A1 | 8/2017 | Goldfarb | |
| 2017/0265994 A1 | 9/2017 | Krone | |
| 2018/0021133 A1 | 1/2018 | Barbarino | |
| 2018/0036119 A1 | 2/2018 | Wei | |
| 2018/0092661 A1 | 4/2018 | Prabhu | |
| 2018/0146964 A1 | 5/2018 | Garcia | |
| 2018/0235657 A1 | 8/2018 | Abunassar | |
| 2018/0242976 A1 | 8/2018 | Kizuka | |
| 2018/0243086 A1 | 8/2018 | Barbarino | |
| 2018/0296329 A1 | 10/2018 | Dixon | |
| 2018/0325671 A1 | 11/2018 | Abunassar | |
| 2018/0344460 A1 | 12/2018 | Wei | |
| 2018/0353181 A1 | 12/2018 | Wei | |
| 2018/0360457 A1 | 12/2018 | Ellis | |
| 2019/0053803 A1 | 2/2019 | Ketai | |
| 2019/0083251 A1 | 3/2019 | Hariton | |
| 2019/0125536 A1 | 5/2019 | Prabhu | |
| 2019/0151041 A1 | 5/2019 | Ho | |
| 2019/0151089 A1 | 5/2019 | Wei | |
| 2019/0159899 A1 | 5/2019 | Marsot | |
| 2019/0167197 A1 | 6/2019 | Abunassar | |
| 2019/0175182 A1 | 6/2019 | Goldfarb | |
| 2019/0183571 A1 | 6/2019 | Eduardo | |
| 2019/0209293 A1 | 7/2019 | Metchik | |
| 2019/0209297 A1 | 7/2019 | Metchik | |
| 2019/0247187 A1 | 8/2019 | Kizuka | |
| 2019/0274831 A1 | 9/2019 | Prabhu | |
| 2019/0321597 A1 | 10/2019 | Van Hoven | |
| 2019/0343630 A1 | 11/2019 | Kizuka | |
| 2019/0350702 A1 | 11/2019 | Hernandez | |
| 2019/0350710 A1 | 11/2019 | Ketai | |
| 2019/0365536 A1 | 12/2019 | Prabhu | |
| 2020/0000473 A1 | 1/2020 | Dell | |
| 2020/0060687 A1 | 2/2020 | Hernández | |
| 2020/0078173 A1 | 3/2020 | Mcniven | |
| 2020/0113678 A1 | 4/2020 | Mccann | |
| 2020/0121460 A1 | 4/2020 | Dale | |
| 2020/0121894 A1 | 4/2020 | Prabhu | |
| 2020/0187942 A1 | 6/2020 | Wei | |
| 2020/0205829 A1 | 7/2020 | Wei | |
| 2020/0245998 A1 | 8/2020 | Basude | |
| 2020/0261107 A1 | 8/2020 | Cohen | |
| 2020/0281591 A1 | 9/2020 | Krone | |
| 2020/0323528 A1 | 10/2020 | Khairkhahan | |
| 2020/0323549 A1 | 10/2020 | Goldfarb | |
| 2020/0323634 A1 | 10/2020 | Von Oepen | |
| 2020/0360018 A1 | 11/2020 | Dell | |
| 2020/0367871 A1 | 11/2020 | Van Hoven | |
| 2021/0015614 A1 | 1/2021 | Kizuka | |
| 2021/0106419 A1 | 4/2021 | Abunassar | |
| 2021/0145574 A1 | 5/2021 | Childs | |
| 2021/0186698 A1 | 6/2021 | Abunassar | |
| 2024/0374386 A1 | 11/2024 | Catania | |

FOREIGN PATENT DOCUMENTS

| | | |
|---|---|---|
| CN | 207368927 | 5/2018 |
| CN | 114176837 A | 3/2022 |
| CN | 216221859 U | 4/2022 |
| CN | 115300181 A | 11/2022 |
| EP | 0558031 B1 | 4/1999 |
| EP | 1383448 A2 | 1/2004 |
| EP | 1383448 B1 | 6/2008 |
| FR | 2768324 A1 | 3/1999 |
| FR | 2768325 B1 | 11/1999 |
| JP | 2008517732 A | 5/2008 |
| JP | 6732663 B2 | 7/2020 |
| WO | 9101689 A1 | 2/1991 |
| WO | 9212690 A1 | 8/1992 |
| WO | 94018893 A1 | 9/1994 |
| WO | 9632882 A1 | 10/1996 |
| WO | 9727807 A1 | 8/1997 |
| WO | 9807375 A1 | 2/1998 |
| WO | 9907354 A2 | 2/1999 |
| WO | 9913777 A1 | 3/1999 |
| WO | 9915223 A1 | 4/1999 |
| WO | 0003759 A2 | 1/2000 |
| WO | 0060995 A2 | 10/2000 |
| WO | 0128432 A1 | 4/2001 |
| WO | 03020179 A1 | 3/2003 |
| WO | 03049619 A2 | 6/2003 |
| WO | 2015057289 A1 | 4/2015 |
| WO | 2016099650 A1 | 6/2016 |
| WO | 2016178722 A1 | 11/2016 |
| WO | 2018093663 A1 | 5/2018 |
| WO | 2019129024 | 7/2019 |
| WO | 2021011531 A1 | 1/2021 |
| WO | 2021027588 A1 | 2/2021 |

* cited by examiner

TUNABLE FIXATION DEVICE

CROSS-REFERENCE TO RELATED APPLICATIONS

This application claims the benefit of the filing date of U.S. Provisional Application No. 63/384,343, filed Nov. 18, 2022, the disclosure of which is hereby incorporated by reference.

BACKGROUND OF THE INVENTION

Field of the Disclosed Subject Matter

The disclosed subject matter relates generally to medical methods, devices, and systems. In particular, the disclosed subject matter relates to methods, devices, and systems for the endovascular, percutaneous or minimally invasive surgical treatment of bodily tissues, such as tissue approximation or valve repair. More particularly, the disclosed subject matter relates to repair of valves of the heart, such as the mitral valve and the tricuspid valve, and venous valves.

Surgical repair of bodily tissues can involve tissue approximation and fastening of such tissues in the approximated arrangement. When repairing valves, tissue approximation includes coapting the leaflets of the valves in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall can be damaged or otherwise dysfunctional. Commonly, the valve annulus can be damaged, dilated, or weakened limiting the ability of the mitral valve to close adequately against the high pressures of the left ventricle.

Tricuspid valve regurgitation has several causes. Functional tricuspid valve regurgitation (FTR) is characterized by structurally normal tricuspid valve leaflets that are nevertheless unable to properly coapt with one another to close properly due to other structural deformations of surrounding heart structures. For example, the right ventricle can become dilated as a result of pulmonary hypertension or an abnormal heart muscle condition (cardiomyopathy).

Other causes of tricuspid valve regurgitation are related to degenerative valves and/or defects of the tricuspid valve leaflets, tricuspid valve annulus, or other tricuspid valve structures. In some circumstances, tricuspid valve regurgitation is a result of infective endocarditis, blunt chest trauma, rheumatic fever, Marfan syndrome, carcinoid syndrome, improper placement of pacemaker leads, or congenital defects to the structure of the heart.

Tricuspid valve conditions are also often associated with problems related to the left side of the heart, such as mitral valve regurgitation. In particular, FTR is often associated with left heart pathologies, though the tricuspid valve is typically left untreated during left heart surgeries. Left heart pathologies such as mitral valve regurgitation and stenosis can induce pressure and volume overload in the right ventricle, which in turn can induce ventricle enlargement and tricuspid annular dilation. Though often relatively mild at the time of treatment of the left heart, this annular dilation of the tricuspid valve can be progressive and asymmetric, and FTR can become more severe as time goes on. Reoperation for repair of the tricuspid valve is often needed owing to the degenerative character of the pathology.

DESCRIPTION OF RELATED ART

Treatments for mitral valve and tricuspid valve regurgitation rely on valve replacement or repair including leaflet and annulus remodeling, the latter generally referred to as valve annuloplasty. Another technique for valve repair, which relies on suturing adjacent segments of the opposed valve leaflets together is referred to as the "bow-tie" or "edge-to-edge" technique. Preferably, the use of devices and systems should not require open chest access and, rather, be capable of being performed either endovascularly, i.e., using devices, such as a catheter, which are advanced to the heart from a point in the patient's vasculature remote from the heart. Furthermore, such devices and systems should allow for repositioning and optional removal of a fixation device (i.e., valve repair clip) prior to fixation to ensure optimal placement. Such devices and systems likewise can be useful for repair of tissues in the body other than heart valves.

BRIEF SUMMARY OF THE DISCLOSURE

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a fixation device for treating a patient.

In accordance with the disclosed subject matter, a tunable fixation device for fixation of leaflets of a heart valve is provided. The fixation device includes a central assembly, at least one arm moveably coupled to the central assembly to be moveable between a closed position and an open position, and at least one gripping element moveable relative to the at least one arm to capture a native leaflet therebetween. The at least one arm includes a body portion having a first end and a second end and a longitudinal axis defined therebetween and a transverse axis perpendicular to the longitudinal axis. The at least one arm further includes a wire frame coupled to the body portion, the wire frame having a first wire segment, a second wire segment, and an interconnection portion interconnecting the first wire segment to the second wire segment, the interconnection portion slidingly engaged with the body portion. The first wire segment is configured to deform upon force applied to the second wire segment by sliding movement of the interconnection portion relative to the body portion, and the second wire segment is configured to deform upon force applied to the first wire segment by sliding movement of the interconnection portion relative to the body portion.

Further in accordance with the disclosed subject matter, the wire frame can have a maximum first condition arm lateral cross-dimension with the wire frame in a first condition, and the wire frame can have a maximum second condition arm width with the wire frame in a second condition. The maximum second condition arm width can be greater than the maximum first condition arm lateral cross-dimension. The wire frame can be configured to slide longitudinally outwardly through the second end of the body portion towards the first condition and decrease in width and elongate in length, and slide longitudinally inwardly through the second end of the body portion towards the second condition and increase in width and decrease in length. The wire frame can be biased towards the first condition and configured to move towards the second condition when the second wire segment is pushed longitudinally inwardly from an external force. The wire frame can be biased towards the second condition and configured to move towards the first condition when the first wire segment is pushed transversely inwardly from an external force. The first wire segment can include a plurality of wire segments. The interconnection portion can include a plurality of interconnection portions.

Furthermore, the maximum first condition arm lateral cross-dimension can be less than an inner diameter of a interventional catheter configured to deliver the tunable fixation device, and the maximum second condition arm width can be greater than the inner diameter of the interventional catheter. The body portion can have at least one coupling slot configured to couple the at least one arm to a leg. An end of the leg can slide longitudinally within the at least one coupling slot. The end of the leg can be tunable between a lowered position and raised position. The wire frame can be coupled to the end of the leg. When the end of the leg is in a raised position, the wire frame can have a maximum second condition arm width. When the end of the leg is in a lowered position, the wire frame has a maximum first condition arm lateral cross-dimension. The maximum second condition arm width can be greater than the maximum first condition arm lateral cross-dimension. The width of the wire frame can be tunable by a user between the maximum first condition arm lateral cross-dimension and the maximum second condition arm width on a user-selected position of the second end of the arm between the lowered position and the raised position. The coupling between the wire frame and the end of the leg can be a slidable coupling. The coupling between the wire frame and the end of the leg can be a fixed coupling.

In accordance with another aspect of the disclosed subject matter, the body portion can include a size adapter and the interconnection portion can be slidingly engaged with the size adapter of the body portion. The size adapter can extend longitudinally beyond the second end of the body portion. The interconnection portion can extend beyond the length of the second end of the body portion. The wire frame can include a single piece structure formed of Nitinol. The wire frame can include non-round wire. The wire frame can include a sheet or strip of an elastic material. The maximum first condition arm lateral cross-dimension can be less than an inner diameter of a interventional catheter configured to deliver the tunable fixation device, and the maximum second condition arm width can be greater than the inner diameter of the interventional catheter. Other objects and advantages of the disclosed subject matter will become apparent from the detailed description to follow, together with the accompanying drawings.

DETAILED DESCRIPTION

Figure 1:
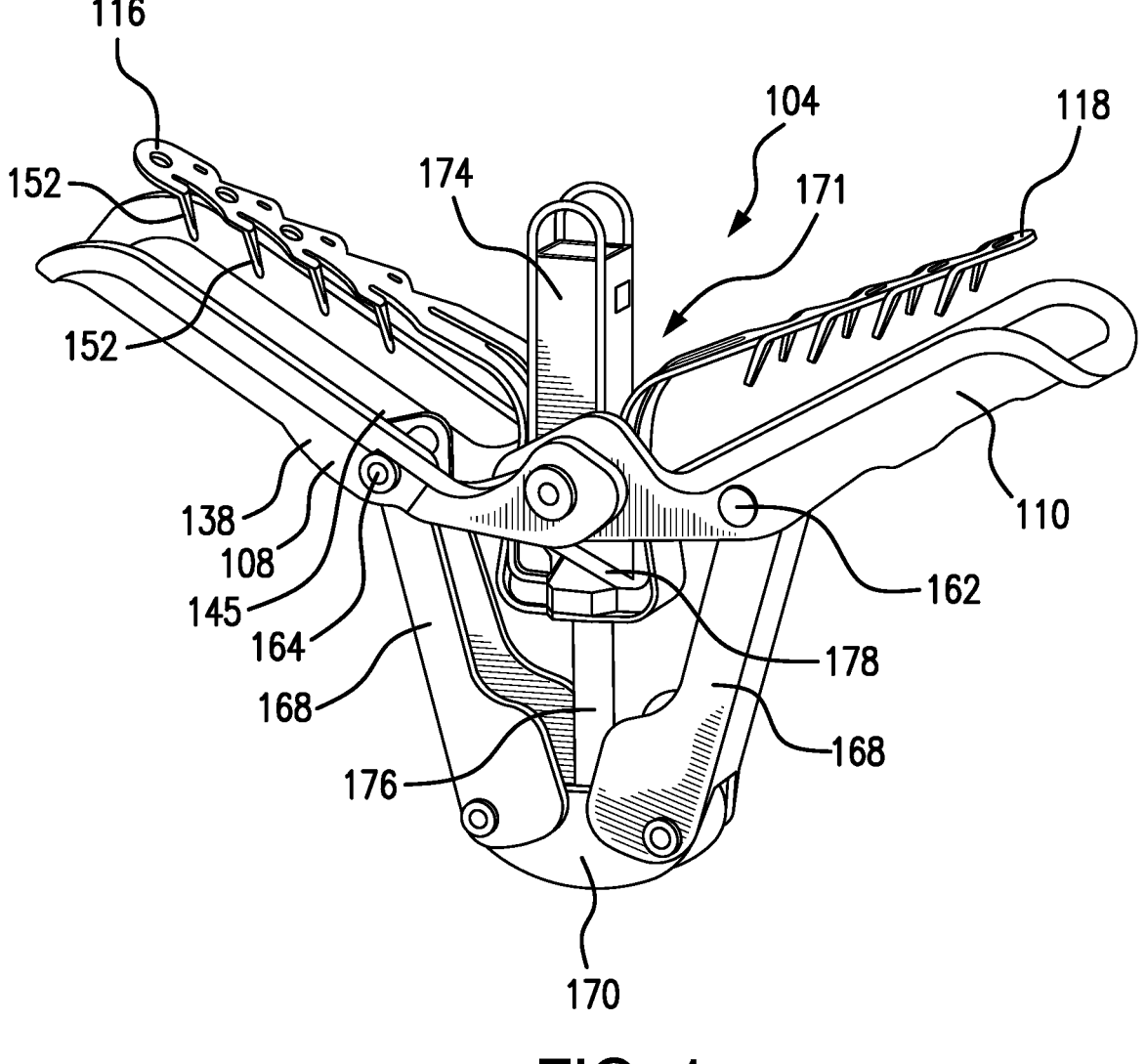
FIG. 1 is a perspective view of an exemplary embodiment of a fixation device for use in accordance with the disclosed subject matter.

Reference will now be made in detail to the various exemplary embodiments of the disclosed subject matter, exemplary embodiments of which are illustrated in the accompanying drawings.

The fixation device for use with the disclosed subject matter provides an edge-to-edge transcatheter valve repair option for patients having various conditions, including regurgitant mitral valves or tricuspid valves. Transcatheter (e.g., trans-septal) edge-to-edge valve repair has been established using a fixation device, such as the MitraClip® Transcatheter Mitral Valve Repair device and the TriClip® Transcatheter Tricuspid Valve Repair device. These fixation devices generally are configured to capture and secure opposing native leaflets using two types of leaflet contacting elements. The first element is a sub-valvular arm (also known as a distal element or fixation element) to contact the ventricular side of a native leaflet to be grasped. With the arm positioned underneath to stabilize the native leaflet in a beating heart, a second gripping element (e.g., a proximal element) can be lowered or moved toward the arm and into contact with the atrial side of the native leaflet to capture the leaflet therebetween. Once each native leaflet is captured by a respective arm and gripping element, the fixation device can be closed by raising or moving the arms toward a center of the fixation device such that the leaflets are brought into coaptation, which results in a reduction in valvular regurgitation during ventricular systole. Furthermore, a covering can be provided on the arms and/or gripping elements to facilitate tissue ingrowth with the captured leaflets.

Additional details of exemplary fixation devices in accordance with the disclosed subject matter are set forth below. Furthermore, a number of patents and publications disclose additional details and aspects of such fixation devices and related operations. See for example, U.S. Pat. No. 7,226,467 to Lucatero et al.; U.S. Pat. No. 7,563,267 to Goldfarb et al.; U.S. Pat. No. 7,655,015 to Goldfarb et al.; U.S. Pat. No. 7,736,388 to Goldfarb et al.; U.S. Pat. No. 7,811,296 to Goldfarb et al.; U.S. Pat. No. 8,057,493 to Goldfarb et al.; U.S. Pat. No. 8,303,608 to Goldfarb et al.; U.S. Pat. No. 8,500,761 to Goldfarb et al.; U.S. Pat. No. 8,734,505 to Goldfarb et al.; U.S. Pat. No. 8,740,920 to Goldfarb et al.; U.S. Pat. No. 9,510,829 to Goldfarb et al.; U.S. Pat. No. 7,635,329 to Goldfarb et al.; U.S. Pat. No. 11,065,119 to Abunassar et al., U.S. Patent Application Publication No. 2017/0042546 to Goldfarb et al.; U.S. Patent Application Publication No. 2017/0239048 to Goldfarb et al.; U.S. Patent Application Publication No. 2021/0186698 to Abunassar et al.; and U.S. Provisional Patent Application No. 63/182,167 filed Apr. 30, 2021, the entirety of the contents of each of these patents and published applications is incorporated herein by reference.

In grasping tissue and leaflet capture for mitral and tricuspid valve disease, certain patient conditions and anatomies, such as those associated with larger dynamic gaps between leaflet tips, can create challenges for capture. As such, there is an opportunity for a fixation device capable of bridging larger gaps, such as in functional mitral regurgitation (FMR) and functional tricuspid regurgitation (FTR), while also providing more reliable leaflet capture, for example in cases of dynamic, chaotic, or overly severe degenerative mitral regurgitation (DMR), such as in cases of Barlow's Syndrome, and severe degenerative tricuspid regurgitation (DTR), such as in the case of Ebstein's Anomaly. Particularly, the size and configuration of the arm of the fixation device can significantly improve performance. However, such modifications can be configured to account for numerous factors to produce desired clinical benefit and still be deliverable transvascularly through an interventional catheter. For example, a typical interventional catheter size for delivery can have an inner diameter of about 0.220 inches or less. Furthermore, when positioned within a patient, the interventional catheter defines a tortious path through which the fixation device can be delivered. As such, the fixation device can be configured to be capable of such delivery through the corresponding bends and turns of the interventional catheter.

Additionally, and as previously noted, the fixation device can be configured to capture or grasp a leaflet between the arm and the gripping element. When in the closed position, the fixation device can facilitate capture of adjacent leaflets positioned between two arms in the final implanted condition. Such capture can be a function of a contact patch area of the leaflets as defined by the width, length, and configuration of the arms, including an optional arm size adapter. An increased contact patch area can provide a more uniformed distribution of stresses in the grasped leaflets and can increase the radius of curvature of the grasped leaflet, which can help to keep the grasped leaflet intact. Hence, increasing arm width and/or length can increase contact patch area and corresponding leaflet capture. For example, the exemplary wire frames in accordance with the disclosed subject matter herein can provide an increased arm width and/or length, which can provide an increased contact patch area of the leaflets to facilitate leaflet grasping. The wire frames can also have flexibility, such that the wire frames can fit within an interventional catheter, and such that the fixation device can be delivered within the catheter without the need to increase the diameter of the delivery catheter. Additionally, and based on the ultimate placement of the fixation device within a patient anatomy, it may be beneficial for the fixation device to have tunable dimensions, such as length and width dimensions, at the delivery site. A fixation device can be tunable by a user, such as a physician adjusting the fixation device dimensions while monitoring various performance parameters. Additionally or alternatively, a fixation device can be self-tuning, such as wherein the fixation device dimensions adjust on their own in response to certain pressures placed on the device by the patient anatomy at the delivery location.

Generally, and as set forth in greater detail below, the disclosed subject matter provided herein includes a tunable fixation device for fixation of leaflets of a heart valve. The fixation device includes a central assembly, at least one arm moveably coupled to the central assembly to be moveable between a closed position and an open position, and at least one gripping element moveable relative to the at least one arm to capture a native leaflet therebetween. The at least one arm includes a body portion having a first end and a second end and a longitudinal axis defined therebetween and a transverse axis perpendicular to the longitudinal axis. The at least one arm further includes a wire frame coupled to the body portion, the wire frame having a first wire segment, a second wire segment, and an interconnection portion interconnecting the first wire segment to the second wire segment, the interconnection portion slidingly engaged with the body portion. The first wire segment is configured to deform upon force applied to the second wire segment by sliding movement of the interconnection portion relative to the body portion, and the second wire segment is configured to deform upon force applied to the first wire segment by sliding movement of the interconnection portion relative to the body portion.

Figure 2:
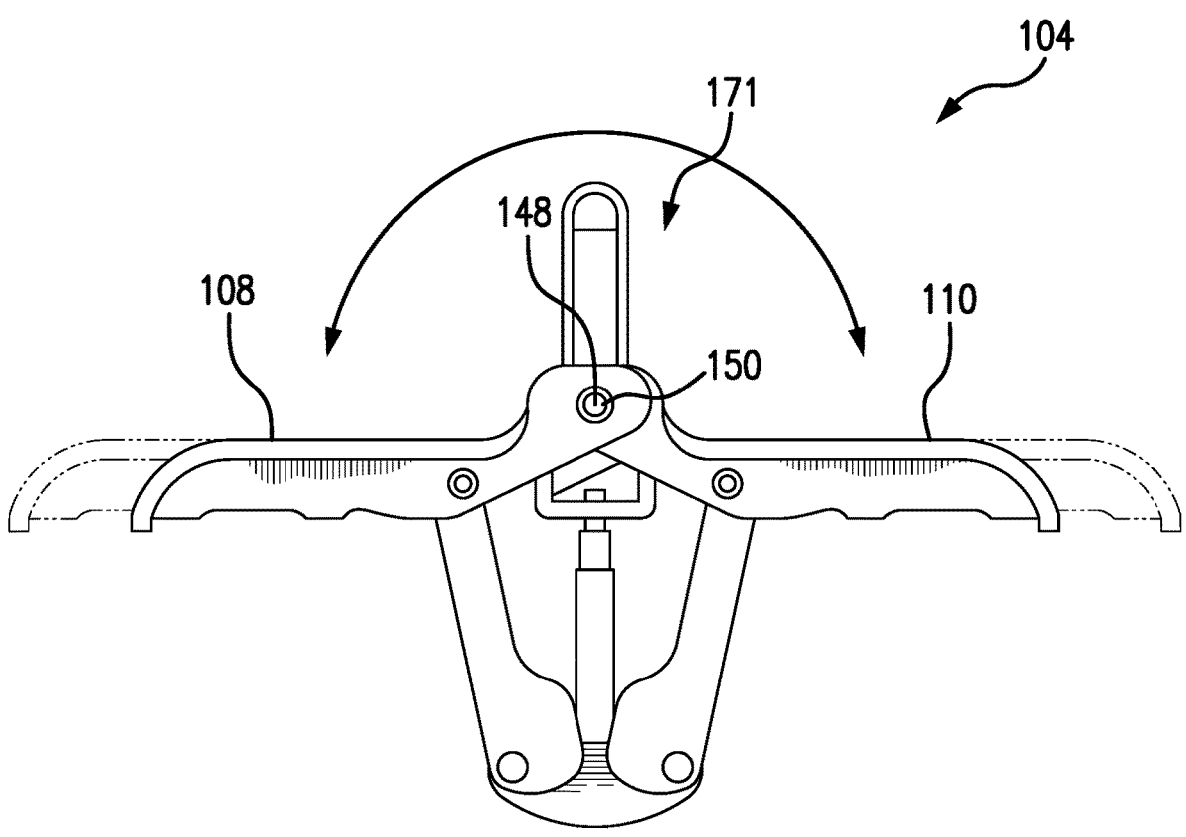
FIG. 2 is a front view of the fixation device of FIG. 1, wherein optional arms of greater length are depicted with dashed lines.

Referring to FIGS. 1-2 for the purpose of illustration and not limitation, a fixation device 104 for fixation of leaflets of a heart valve is disclosed herein. The fixation device 104 as embodied herein includes a central assembly 171. The central assembly 171 can include various central components for operation and release of the fixation device 104, for example, a coupling member 174, as described further in the disclosures of the patents and applications incorporated in their entirety by reference herein. The fixation device 104 as depicted further includes at least one arm 108 moveably coupled relative to the central assembly 171. As shown, the fixation device can further include a second arm 110 moveably coupled relative to the central assembly 171. The at least one arm 108 can be moveably coupled to the central assembly 171 to be moveable between a closed position and an open position. The fixation device as depicted further includes at least one gripping element 116 moveable relative to the at least one arm 108 to grasp and capture a native leaflet therebetween. The fixation device 104 can also include various components for operation of the fixation device, for example, body portion 138, trough 145, frictional elements 152, rivets 164, and gripping elements 116, 118, legs 168, a base 170, a stud 176, and a locking mechanism 178, as described further in the disclosures of the patents and applications incorporated in their entirety by reference herein.

With reference to FIG. 2, for illustration and not limitation, each arm 108, 110 of the fixation device 104 can be rotatable or moved about a respective axis point 148, 150 between closed, open, and inverted positions, as well as any position therebetween. Furthermore, the arms 108, 110 can be selected from a range of suitable lengths, wherein the appropriate length can be selected by the physician or health care provider after inspection of a patient. For purpose of comparison, a first length of each arm 108, 110 is depicted in FIG. 2 in solid lines, and a second longer length of each arm of the disclosed subject matter is depicted in dashed lines. Each arm depicted in solid lines can be an entirely separate arm with a different length as compared to the corresponding arm depicted in dashed lines.

Figures 3A, 3B:
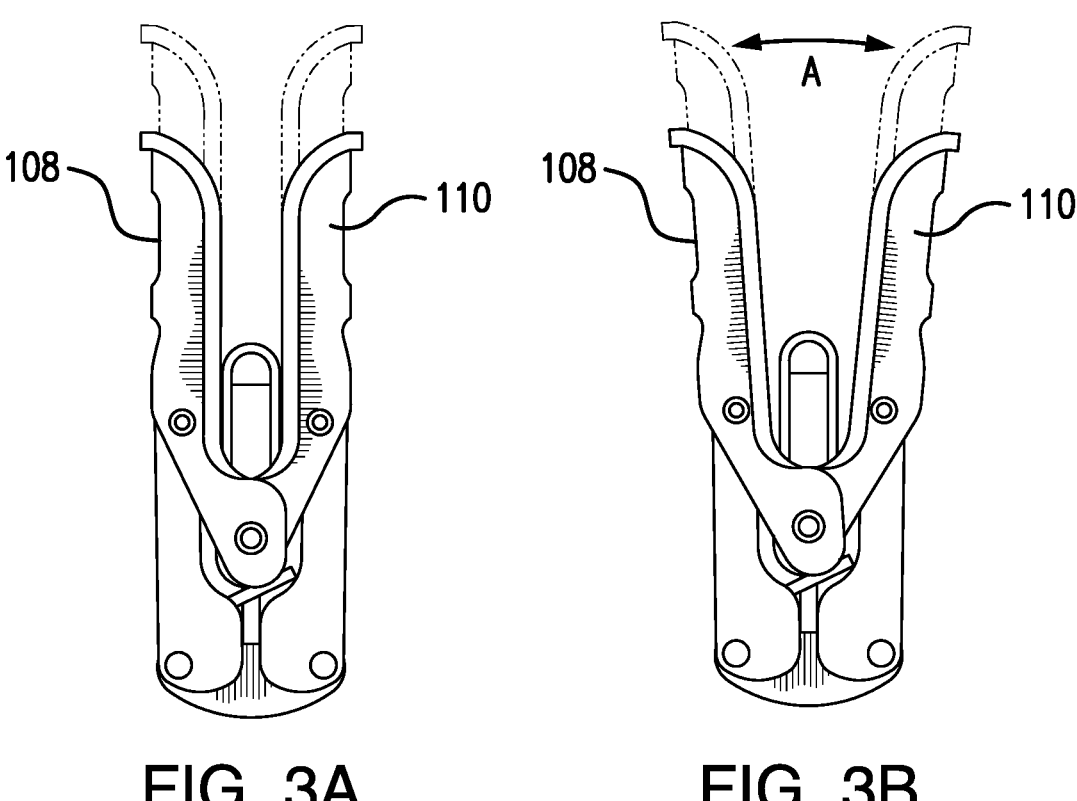
FIGS. 3A-3C are front views of the fixation device of FIG. 1 at various positions, wherein optional arms of greater length are depicted with dashed lines.
Figure 3C:
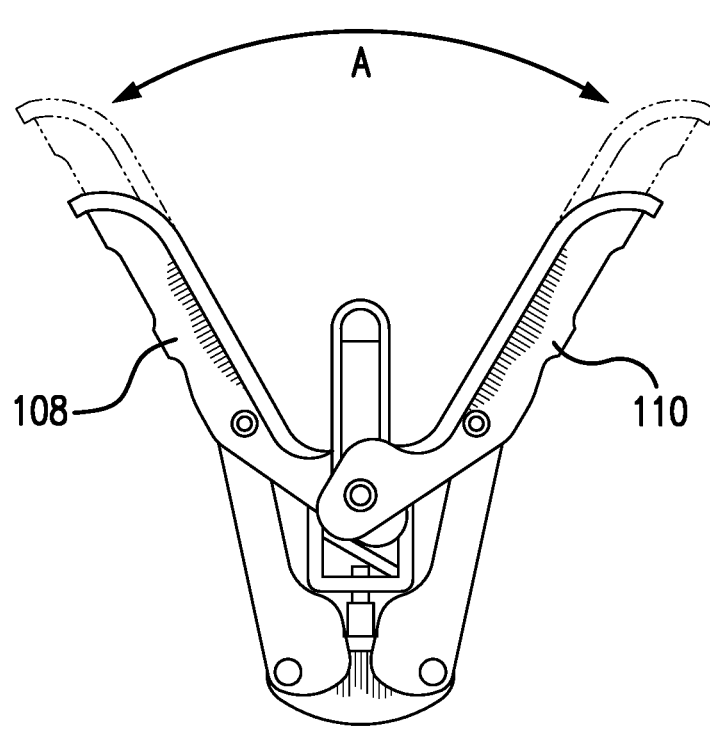

As depicted herein in FIGS. 3A-3C, various positions of the fixation device 104 are depicted for purpose of illustration and not limitation. Arms 108, 110 of longer length are illustrated in dashed lines for comparison to shorter arms. In FIG. 3A, the fixation device is in the closed position, wherein the arms 108, 110 are positioned axially in alignment, e.g., vertically or nearly vertically as shown. FIGS. 3B and 3C illustrate the arms 108, 110 positioned with an angle A between each other. In FIG. 3B, angle A is about 10 degrees and in FIG. 3C angle A is about 60 degrees. As disclosed herein, the fixation device 104 is in the closed position when angle A is about 30 degrees or less, although another angle can result when leaflets of greater thickness are captured therebetween. Although not depicted, the arms 108, 110 can continue to open until angle A exceeds 180 degrees, e.g., inverted.

Figures 4A, 4B:
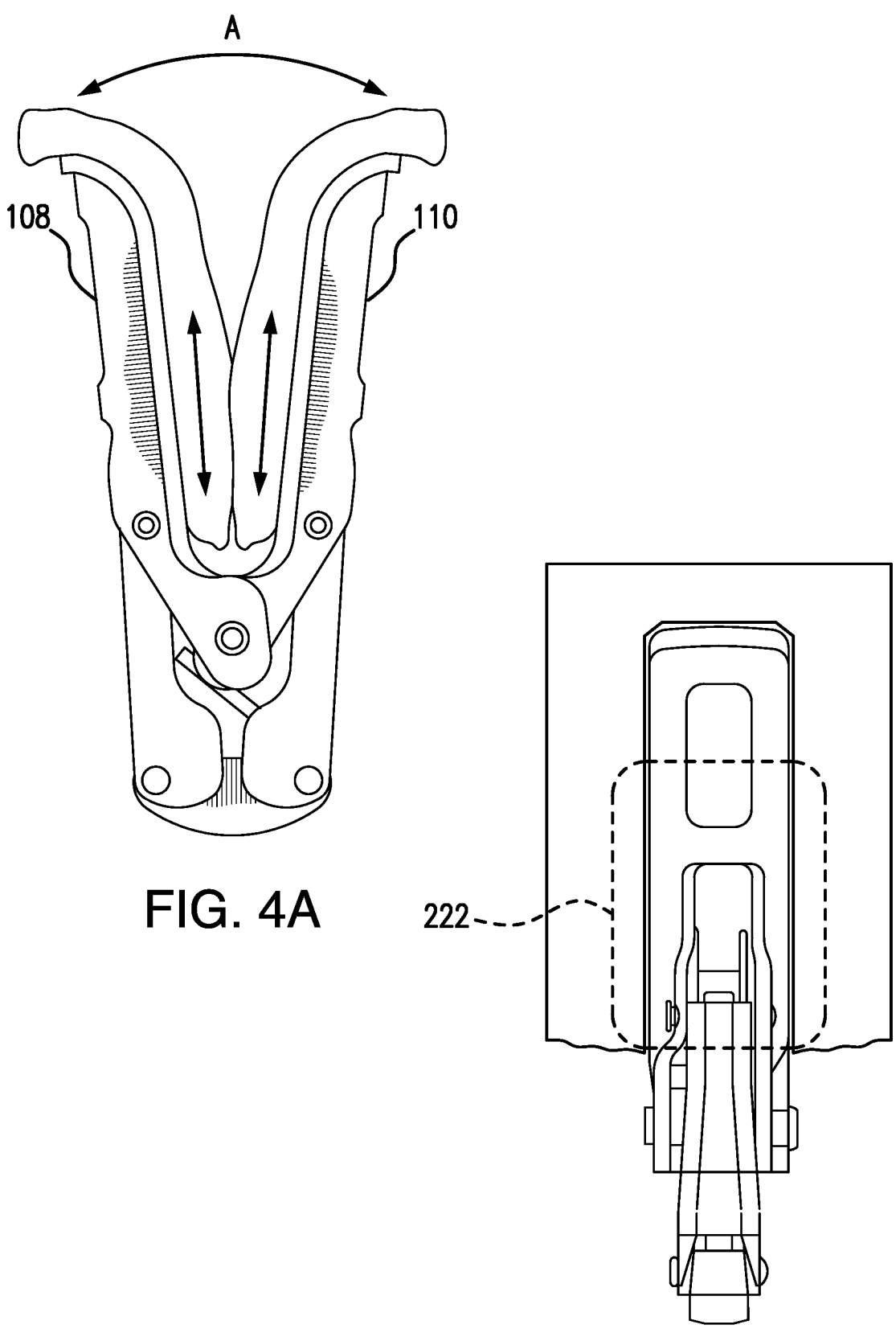
FIG. 4A is a front schematic view of the fixation device of FIG. 1 having leaflets captured therein.
FIG. 4B is a side view of the fixation device of FIG. 1 to schematically depict a contact patch area.

As previously noted generally, and as set forth in further detail below, a native leaflet can be captured between each arm and a respective gripping element. Each arm can then be moved toward its closed position. In this manner, adjacent leaflets can further be captured between two arms in the closed position. For example, and for purpose of illustration and not limitation, FIGS. 4A-4B show the fixation device 104 depicted with the arms 108, 110 at an angle A of about 20 to 30 degrees with two leaflets captured therebetween, wherein each leaflet is captured between an arm and a respective gripping element (wherein the gripping element is not shown for clarity). As illustrated in FIG. 4B, a contact patch 222 depicted in dashed lines is defined by the area of tissue contact between the arms 108, 110 and corresponding size adapters. The contact patch area 222 represents a tissue-to-tissue contact patch area defined by the area of a leaflet in contact with a counterpart leaflet. The angle A can affect the contact patch area 222, wherein a reduced angle A can increase the contact patch area 222, and likewise an increased angle A can decrease the contact patch area 222.

Figure 5:
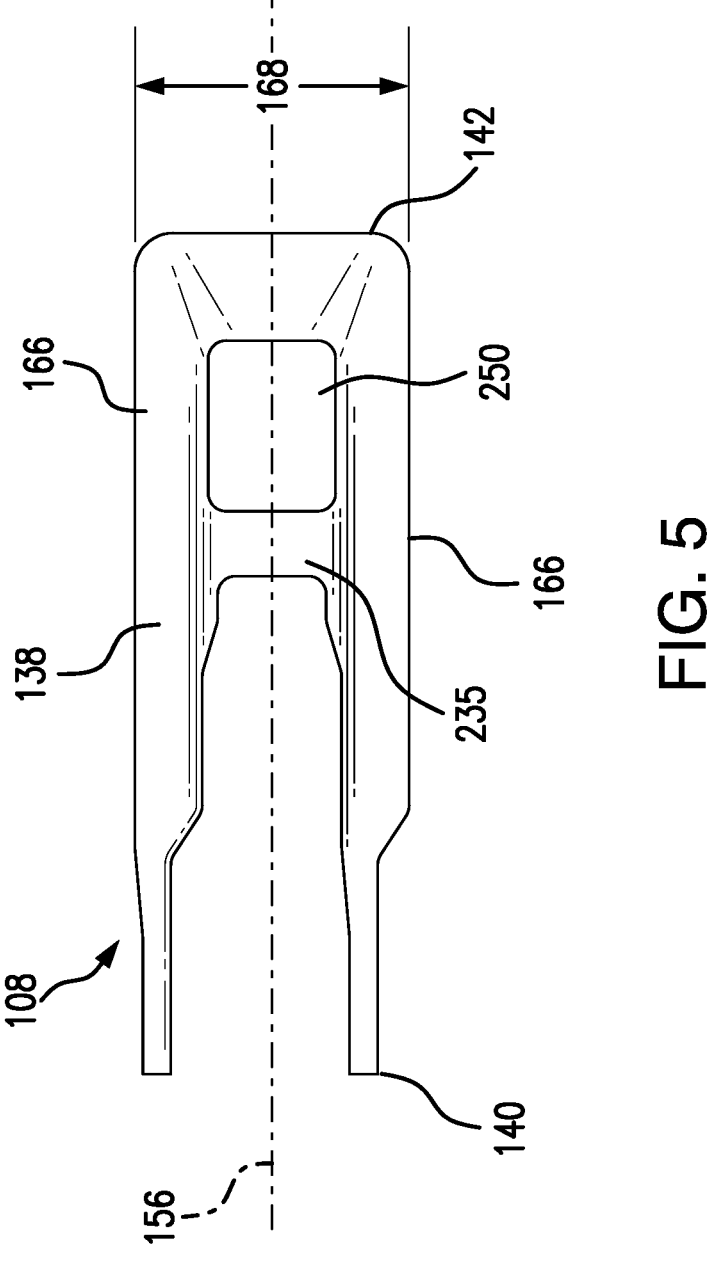
FIG. 5 is a plan view of an exemplary embodiment of an arm in accordance with the disclosed subject matter.

With reference to FIG. 5, the at least one arm 108 includes a body portion 138 having a first end 140 and a second end 142, a longitudinal axis 156 defined therebetween, and a transverse axis 157 perpendicular to the longitudinal axis 156. The second end 142 can be moveable between a closed position and an open position. The body portion 138 has opposing body lateral sides 166, and each body lateral side 166 extends between the first end 140 and the second end 142. The body portion 138 has a body portion width 169 defined between the opposing body lateral sides 166. The at least one arm 108 can include a strut member 235 extending perpendicular to the longitudinal axis 156. The at least one arm can include an aperture 250 and the strut 235 can define one side of the aperture 250.

Figure 6:
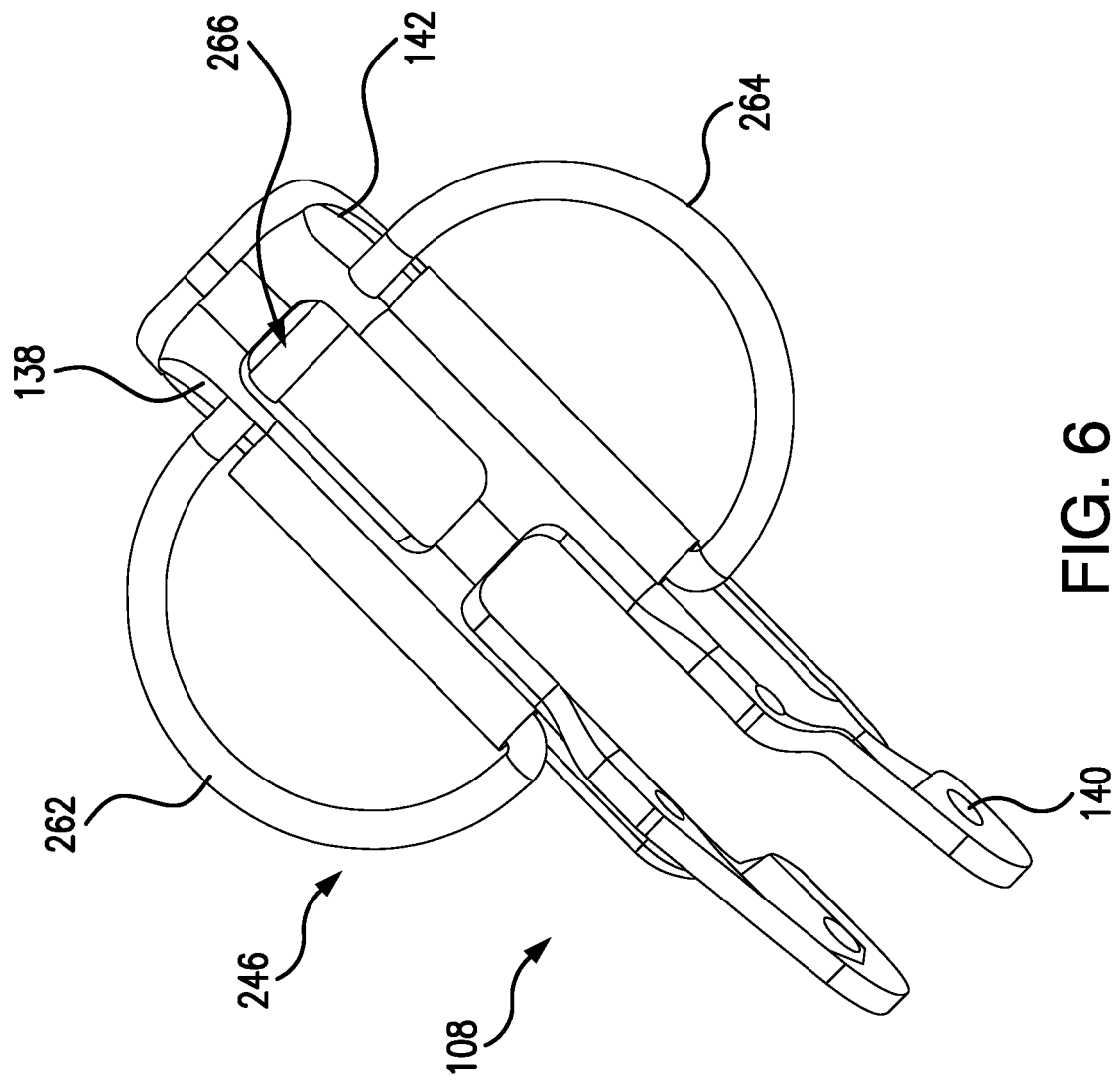
FIG. 6 is a perspective view of an embodiment of an arm having a slidingly engaged wire frame.

In accordance with the disclosed subject matter, the fixation device 104 can be a tunable fixation device. For example, and for purpose of illustration and limitation, FIG. 6 depicts the at least one arm 108 including a wire frame 246 coupled to the body portion 138, the wire frame 246 having a first wire segment 262, a second wire segment 264, and an interconnection portion 266 interconnecting the first wire segment to the second wire segment. The first wire segment 262 and second wire segment 264, as depicted, are secured to opposite sides of body portion 138 and extend laterally outwardly to form respective loops which, in a deployed condition, effectively expand the width of arm 108 such that first and second wire segments 262, 264 define lateral extents of arm 108. The interconnection portion 266 extends between the first and second wire segments 262, 264 and through body portion 138 such that interconnection portion 266 is slidingly engaged with the body portion 138 and is slidable in a transverse direction relative to the longitudinal axis 156 of body portion 138. The first wire segment 262 is configured to deform upon force applied to the second wire segment 264 by sliding movement of the interconnection portion 266 relative to the body portion 138. In this regard, deforming first wire segment 262 decreases the size of the loop formed by the first wire segment 262, and increases the size of the loop defined by the second wire segment 264 such that the lateral extent defined by the second wire segment 264 is positioned further away from the longitudinal axis 156 of the body portion 138 than the lateral extent defined by the first wire segment 262. Similarly, the second wire segment 264 is configured to deform upon force applied to the first wire segment 262 by sliding movement of the interconnection portion 266 relative to the body portion 138. In this regard, deforming second wire segment 264 decreases the size of the loop formed by the second wire segment 264, and increases the size of the loop defined by the first wire segment 262 such that the lateral extent defined by the first wire segment 262 is positioned further away from the longitudinal axis 156 of the body portion 138 than the lateral extent defined by the second wire segment 264. In an undeformed and deployed state, the lateral extents defined by the respective first and second wire segments 262, 264 may be equidistant from the longitudinal axis 156 of body portion 138. The wire frame 246 can be fixed at a location along a length of the body portion 138. For example, opposed ends of wire frame 246 may be fixedly secured to opposite sides of body portion 138 relative to longitudinal axis 156. Such opposed ends of wire frame 246 may be secured via a press-fit, weld, adhesive, or rivet, for example.

For example, if the fixation device 104 is confined on one side by the heart anatomy upon delivery, the wire frame 246 can tune itself via pressure applied by the heart anatomy. For purpose of illustration and not limitation, the first wire segment 262 can deform upon force applied by a heart wall when the fixation device 104 is confined by the heart wall. This deformation of the first wire segment 262 can cause the interconnection portion 266 to slide, relative to the body portion 138 and transverse to the longitudinal axis 156 thereof, towards the side of the second wire segment 264, thus reducing the width of the first wire segment 262 and extending the width of the second wire segment 264 on the opposing side. Alternatively, and depending on the position of the heart anatomy relative to the fixation device 104, the second wire segment 264 can deform upon force applied by a heart wall, and the second wire segment 264 can similarly be reduced in width and the first wire segment 262 can be extended in width. An increased arm width on one side and decreased width on the other side can cause the corresponding contact patch area of the leaflets to be maintained.

Figure 7:
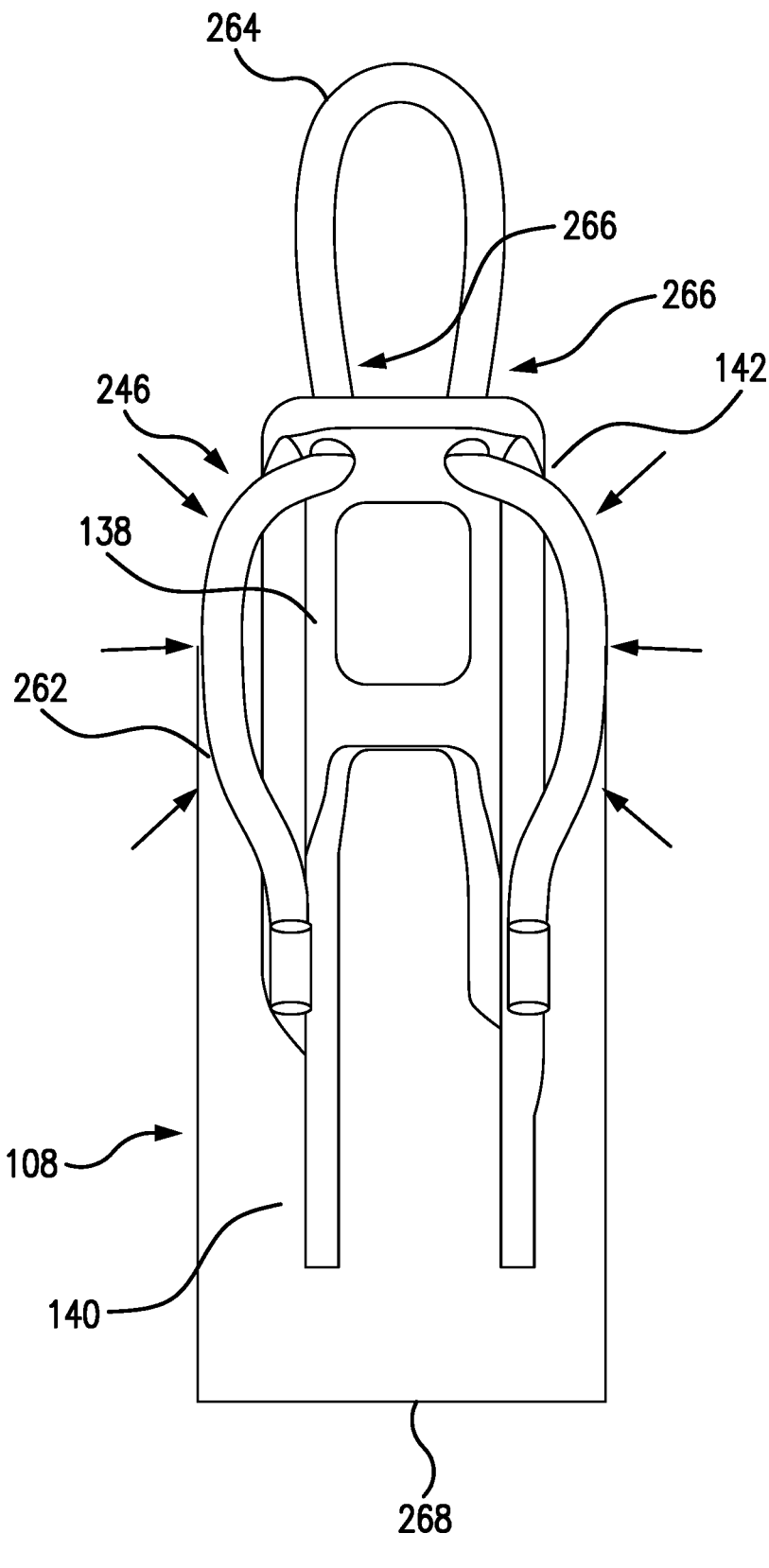
FIG. 7 is a plan view of an arm having an alternative embodiment of a slidingly engaged wire frame in a first condition.
Figure 8:
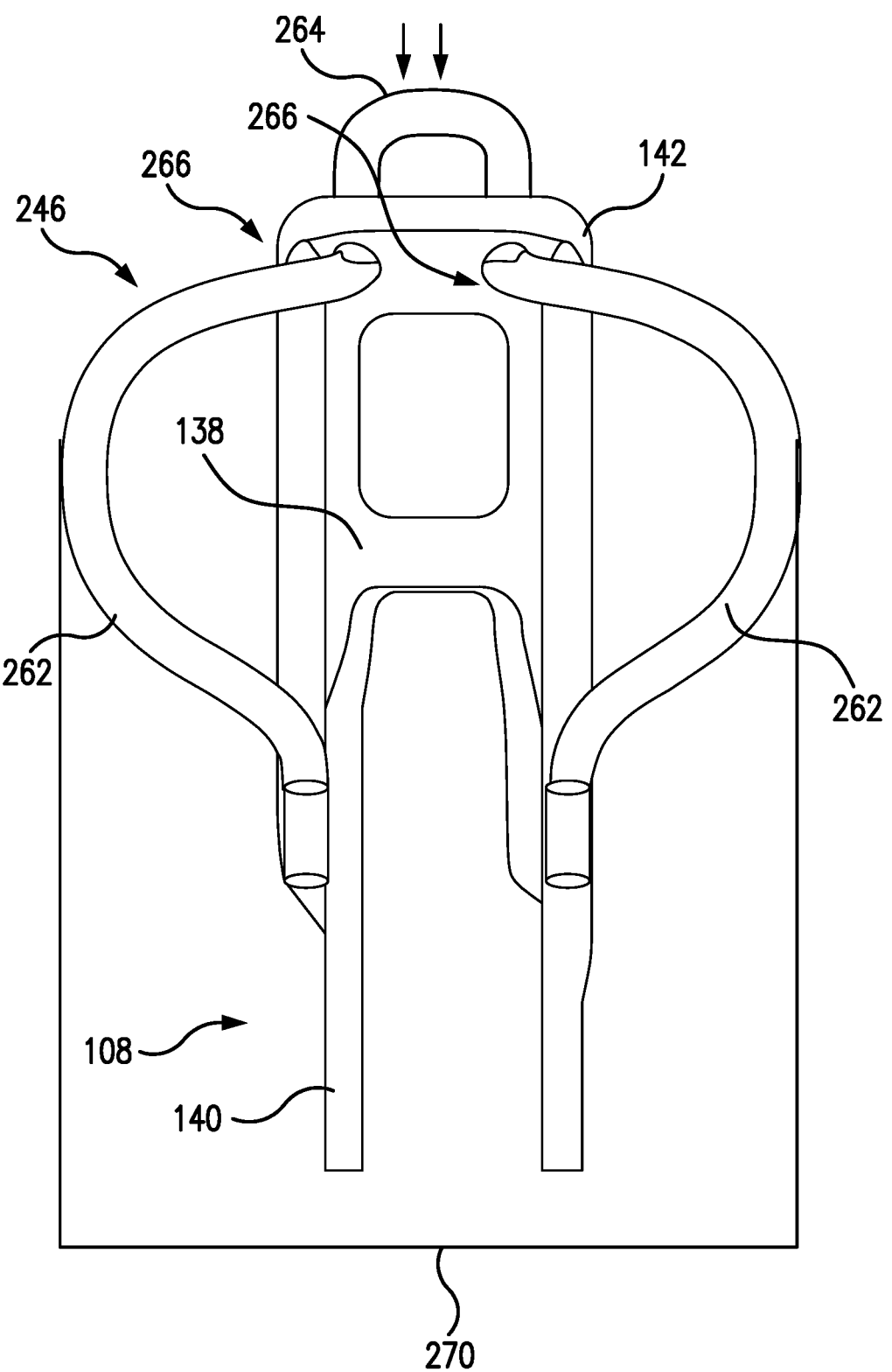
FIG. 8 is a plan view of the arm and wire frame of FIG. 7 having the wire frame in a second condition.

In accordance with an additional aspect of the subject disclosed herein, and with reference to FIGS. 7 and 8, the fixation device 104 can be a self-tuning fixation device. Referring to FIG. 7, for the purpose of illustration and not limitation, the wire frame 246 can have a maximum first condition arm lateral cross-dimension 268 with the wire frame 246 in a first condition or delivery condition. The wire frame 246 can be configured in the first condition when delivered through the catheter, allowing for a reduced or narrow device profile to comply with a corresponding narrow catheter. The delivery condition may be achieved by applying pressure to and deforming both the first and second wire segments 262, 264 inwardly at the same time toward the longitudinal axis 156 such that the interconnection portion 266 projects distally from body portion 138 and beyond a second end 142 thereof, as shown in FIG. 7.

Referring to FIG. 8, for the purpose of illustration and not limitation, the wire frame 246 can have a maximum second condition arm width 270 with the wire frame 246 in a second condition or deployed condition. The maximum second condition arm width 270 can be greater than the maximum first condition arm lateral cross-dimension 268. The wire frame 246 can be configured in the second condition to expand the device profile and provide an increased contact patch area. The deployed condition may be achieved by applying pressure to and deforming the interconnection portion 266 axially toward the second end of body portion 142 which causes first and second wire segments 262, 264 to laterally outwardly expand to their deployed condition, as shown in FIG. 8.

In other words, the wire frame 246 can adjust in geometry and configuration by sliding between the first condition and the second condition. The wire frame 246 can be configured to slide longitudinally outwardly or distally through the second end of the body portion 138 towards the first condition and decrease in width and elongate in length, and slide longitudinally inwardly through the second end of the body portion 138 towards the second condition and increase in width and decrease in length. The wire frame 246 can be biased towards the first condition and configured to move towards the second condition when the second wire segment 264 is pushed longitudinally inwardly from an external force. Alternatively, the wire frame 246 can be biased towards the second condition and configured to move towards the first condition when the first wire segment 262 is pushed transversely inwardly from an external force. The first wire segment 262 can include a plurality of wire segments. The interconnection portion 266 can include a plurality of interconnection portions.

The maximum first condition arm lateral cross-dimension 268 can be less than an inner diameter of an interventional catheter configured to deliver the tunable fixation device 104, and the maximum second condition arm width 170 can be greater than the inner diameter of the interventional catheter. For example, and for purpose of illustration and not limitation, the fixation device 104 can be biased in the first condition, as shown in FIG. 7, to provide a narrower device profile such that the fixation device 104 can fit within an interventional catheter and can be deliverable transvascularly through the bends and turns of the interventional catheter. Upon delivery of the fixation device 104, the second wire segment 264 can be pushed longitudinally inwardly from an external force, such as the presence of a heart wall against the second wire segment 264. Thus, the wire frame 264 can be configured to move towards the second condition, as shown in FIG. 8. The second condition can provide a wider device profile, and can provide an increased contact patch area of the leaflets to facilitate leaflet grasping. Based on the disclosed subject matter having two at least two embodiments, as shown in FIG. 7 and FIG. 8, it is simultaneously advantageous to use for both short and long leaflets, and in cases of dissimilar pairs of leaflets (e.g., where one leaflet is long and the other leaflet is short). When grasping a longer leaflet, the arm length may remain long, as shown in FIG. 7, to maximize the length of leaflet grasped by the device, which is necessary when long leaflets are present in a regurgitant valve. For example, in the edge-to-edge surgical approach, longer stitches would be used for longer leaflets. When grasping of shorter leaflets is being performed, a conventional long device arm will not permit deep leaflet insertion. By contrast in fixation device 104, the leaflet tip can be deeply inserted within the device because the wire segment 264 at the tip may be easily pushed inward to shorten the overall length of the device arm.

Figure 9A:
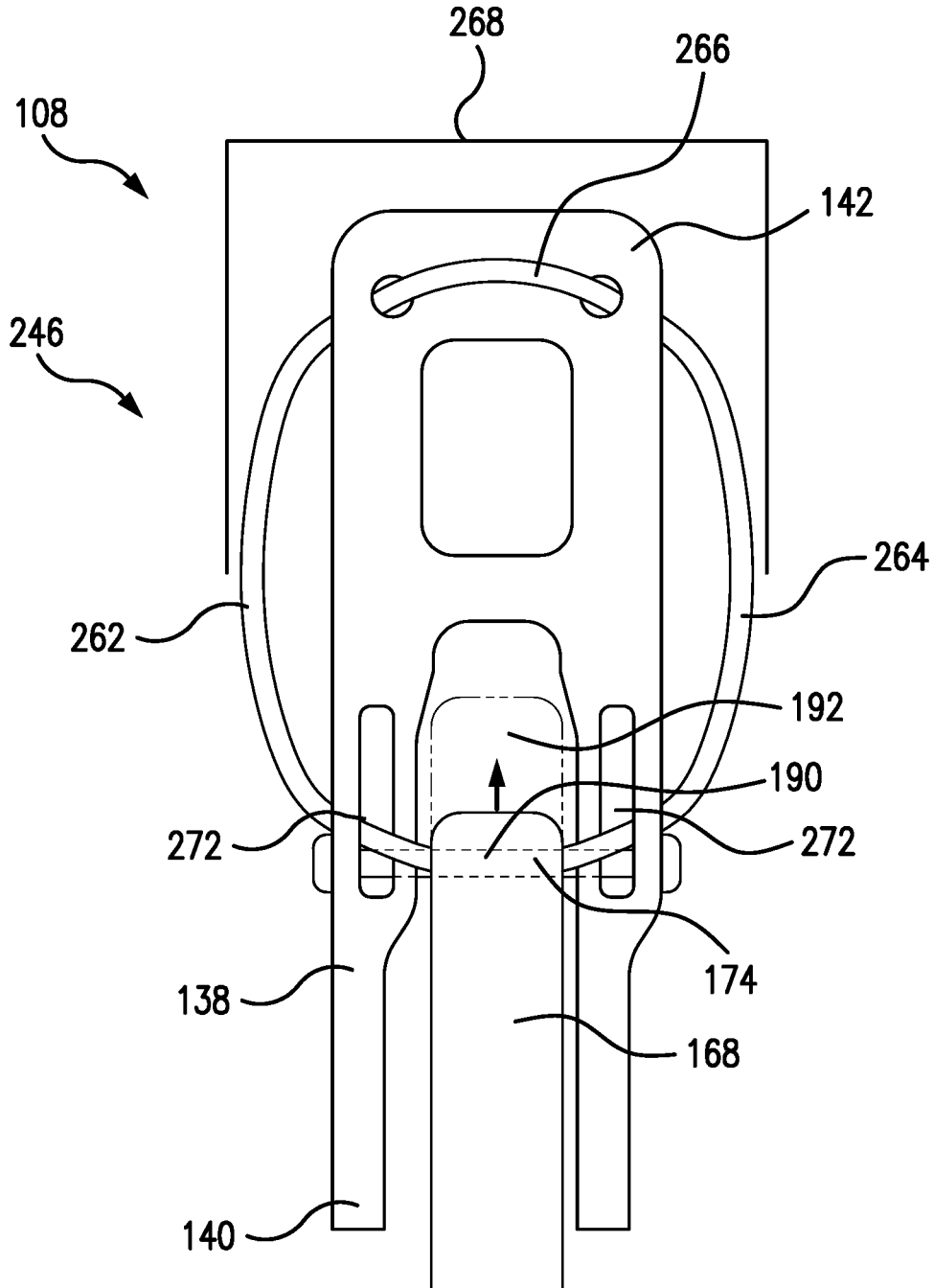
FIG. 9A is a plan view of an embodiment of a leg and a slotted arm having a wire frame in a first condition.
Figure 9B:
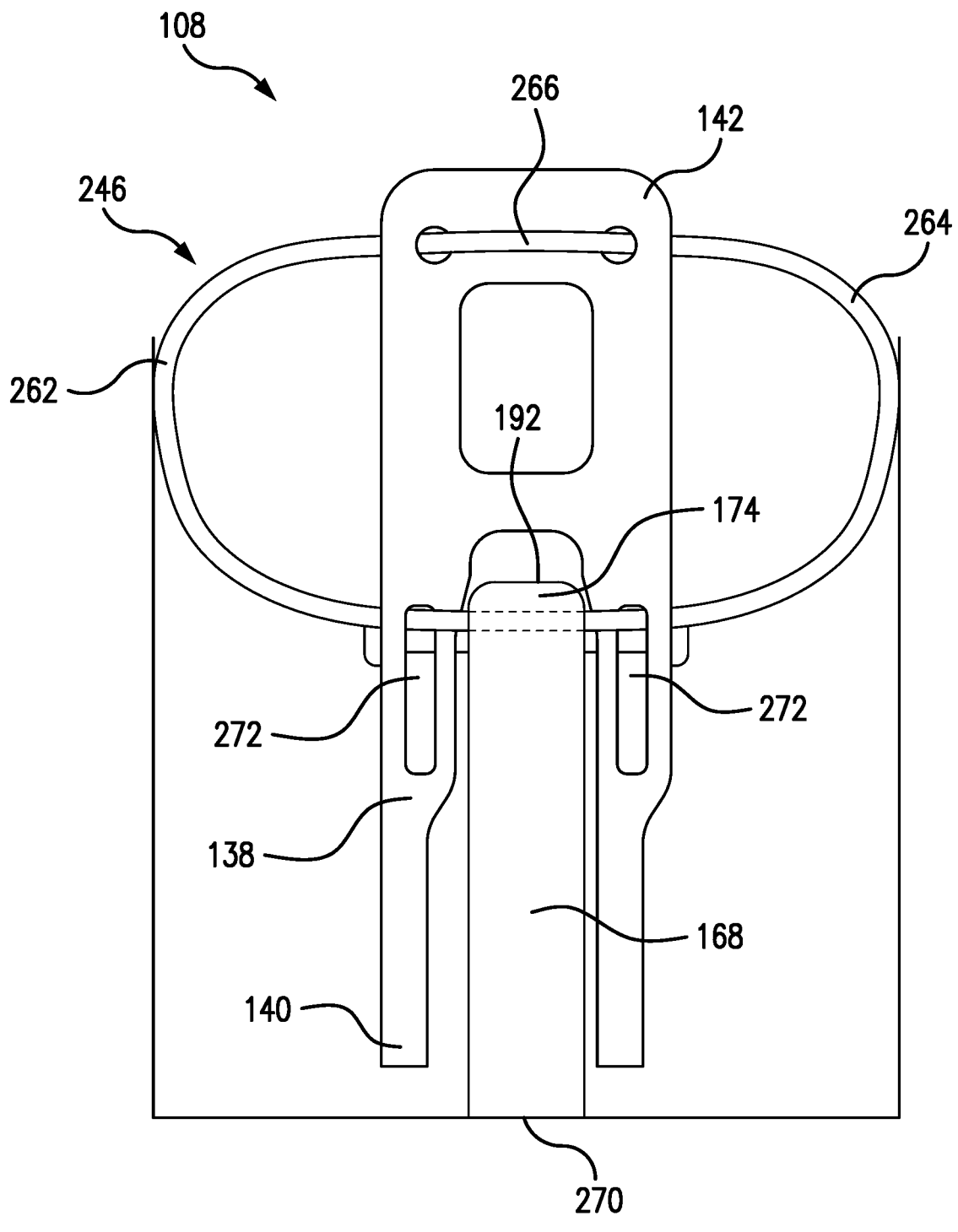
FIG. 9B is a plan view of the arm and leg of FIG. 9A having the wire frame in a second condition.
Figure 10A:
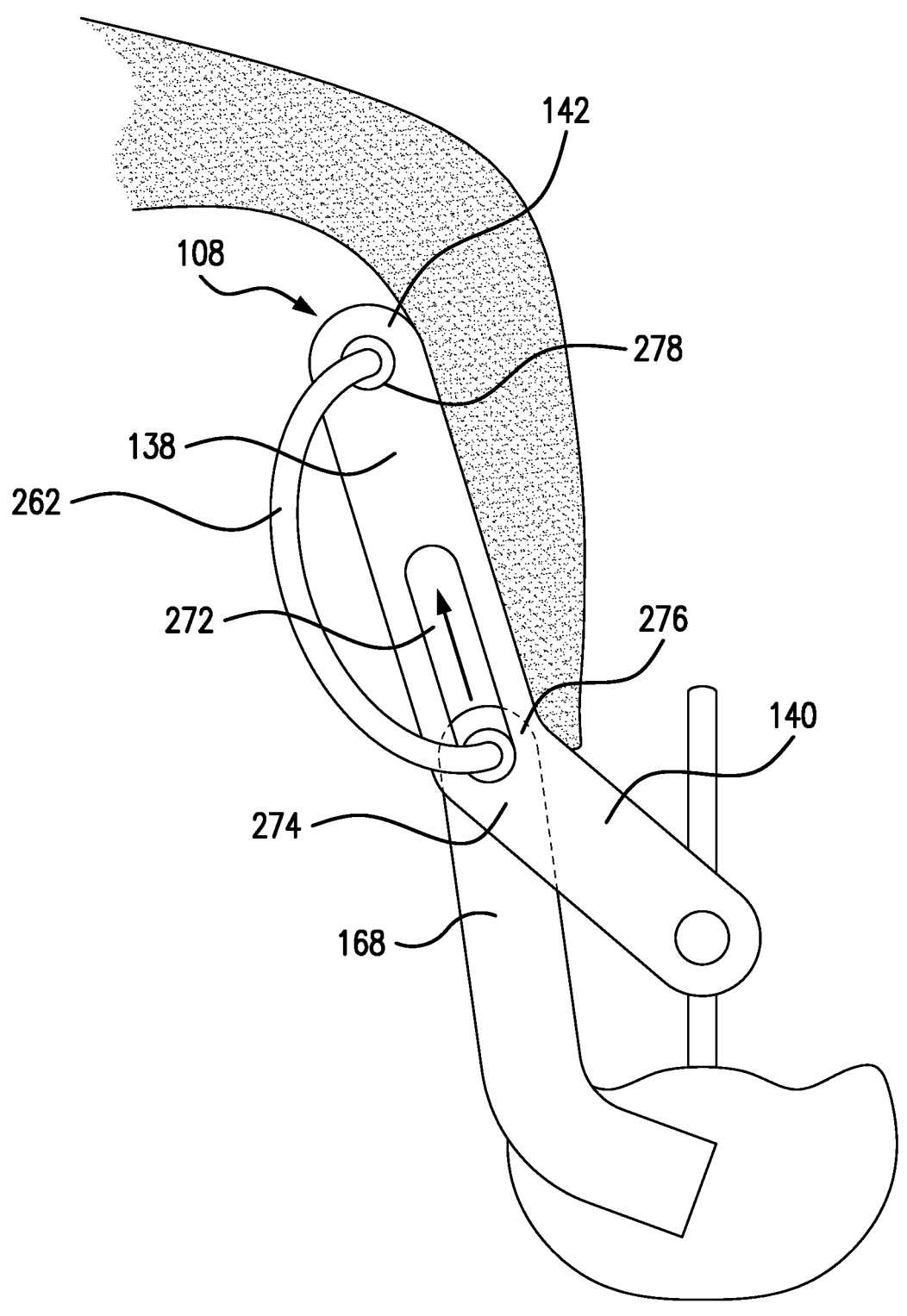
FIG. 10A is a side view of the arm and leg of FIG. 9A.
Figure 10B:
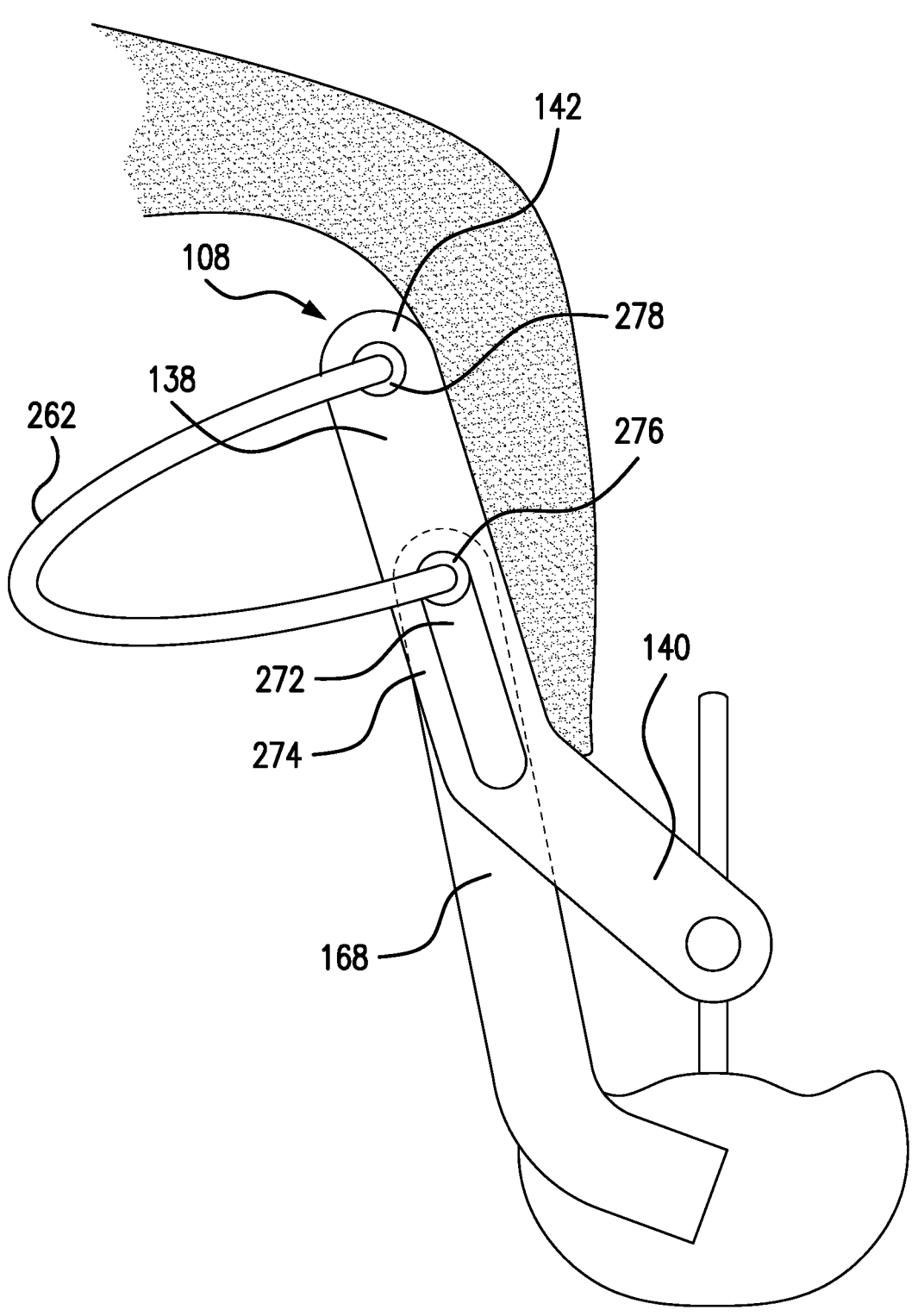
FIG. 10B is a side view of the arm and leg of FIG. 9B.
Figure 11:
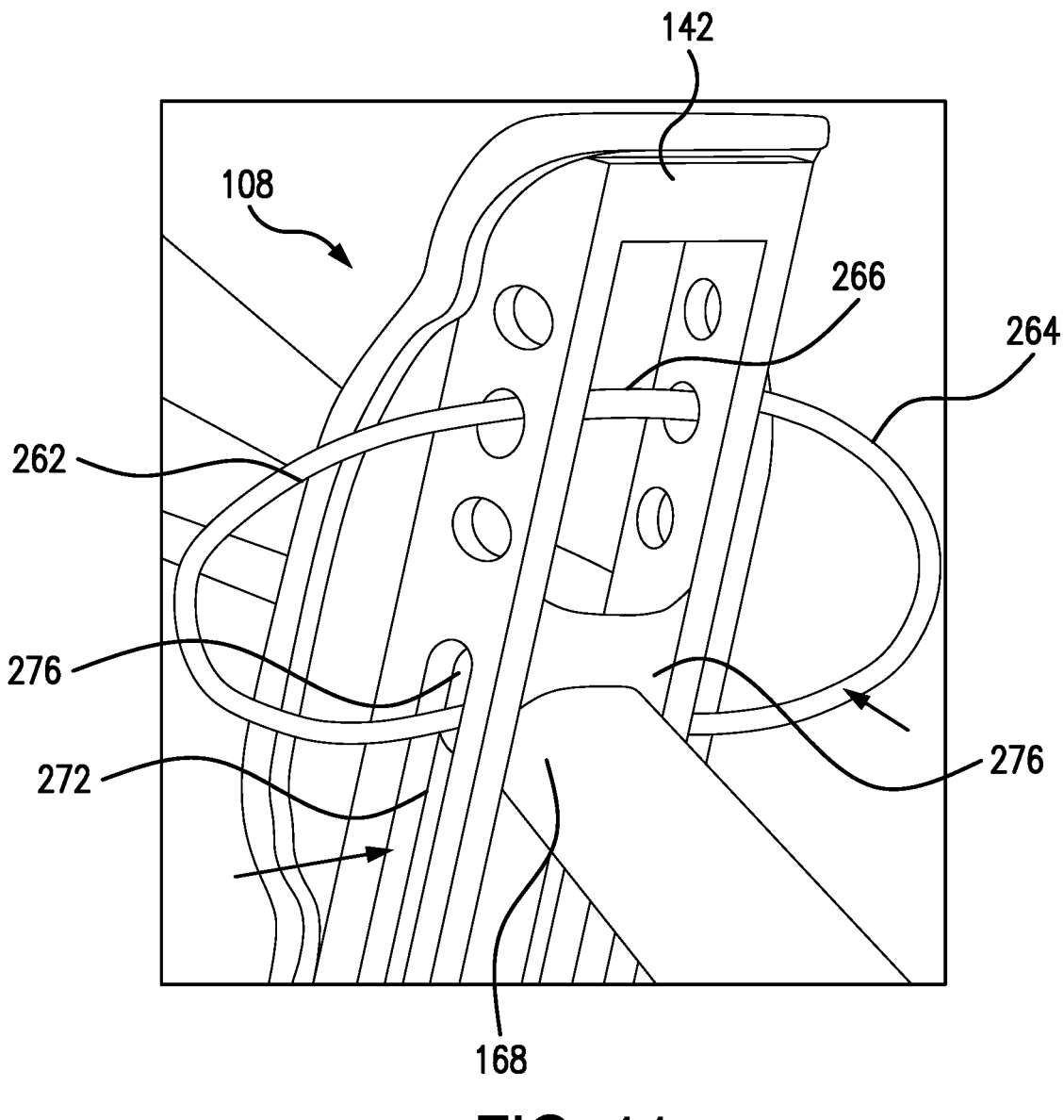
FIG. 11 is a perspective view of the arm and leg of FIG. 9B.
Figure 12A:
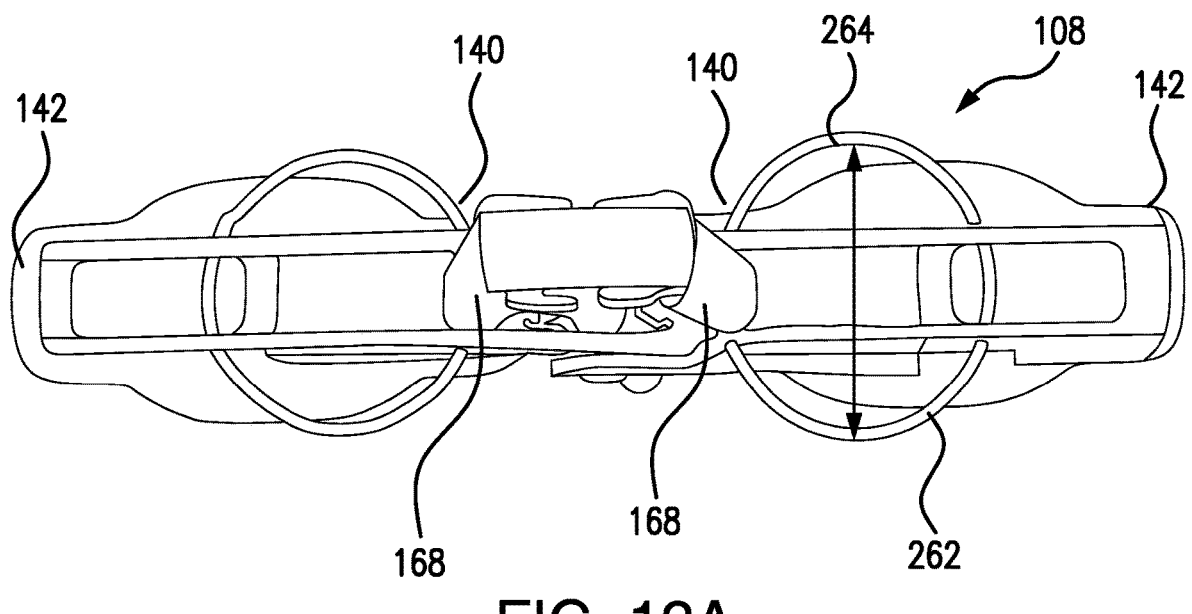
FIG. 12A is a top view of the arm and leg of FIG. 9A.
Figure 12B:
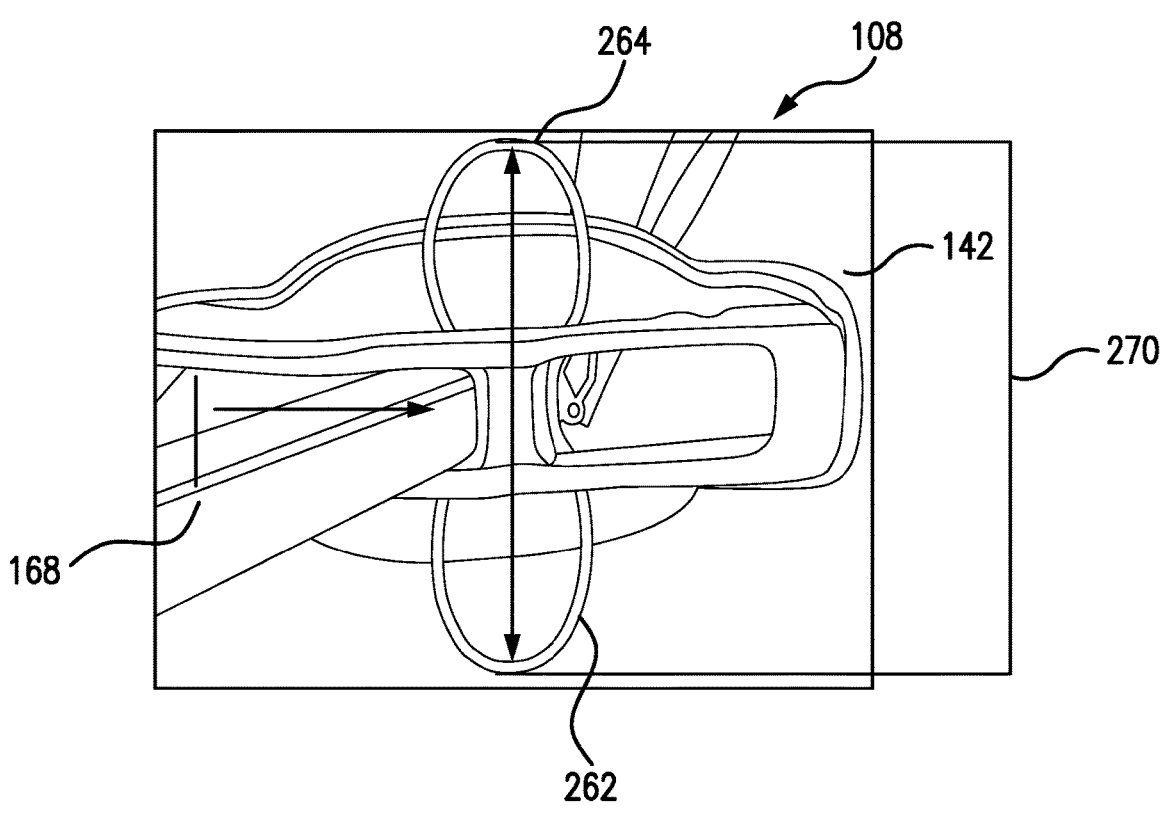
FIG. 12B is a top view of the arm and leg of FIG. 9B.

In accordance with an additional aspect of the subject disclosed herein, and with reference to FIGS. 9A, 10A, 11, and 12A, the body portion 138 can have at least one coupling slot 272 configured to couple the at least one arm 108 arm to a leg 168. An end of the leg 174 can slide 274 longitudinally within the at least one coupling slot 272. The end of the leg 174 can be tunable between a lowered position 190 and raised position 192. When the end of the leg 174 is in a lowered position 190, the wire frame 246 has a maximum first condition arm lateral cross-dimension 268. When the end of the leg 174 is in a raised position 192, the wire frame 246 can have a maximum second condition arm width 270, as shown in FIGS. 9B, 10B, and 12B. During a procedure, the physician can control the leg 168 position when the fixation device 104 is at the implantation site. The physician can also control the amount of force that the leg 168 places against arm 108 when the fixation device is in the closed position. The leg 168 position and force controls the end of the leg 174 between the lowered position 190 and the raised position 192. As such, when the fixation is grasping a leaflet in the closed position, a physician can apply increased force on the leg 168 against the arm 108, which can move the end of the leg 172 toward the raised position 192 and widen the wire frame 246. A physician can measure the influence of the widened wire frame 246 on certain parameters, such as the valve gradient (the difference in pressure on each side of the valve), and determine if the wire frame 246 should be further adjusted. As such, during a minimally invasive valve repair procedure a physician can control the position of the end of the leg 172 within the coupling slot 272 and thus can increase or decrease the arm lateral cross-dimension of the wire frame such that the fixation device can increase the contact patch area.

It should be noted that, in this embodiment, the wire frame 246 is still tunable in situ, as described above, as the interconnection portion 266 is slidable upon deformation of the first wire segment 262 or second wire segment 264. In other words, wire frame 246 may form a closed loop in which a first end of the loop is connected to leg 172 and passes through slots 272, a second end of the loop forms the interconnection portion 266 and extends transversely through body portion 138, such as through openings thereof, and first and second sides of the loop extending between these ends form the respective first and second wire segments 262, 264, as best shown in FIG. 9B. Wire frame 246 may also slide through slots 272 and leg 174 upon deformation of one of first and second wire segments 262, 264 to further facilitate tuning.

The maximum second condition arm width 270 can be greater than the maximum first condition arm lateral cross-dimension 268. The width of the wire frame 246 can be tunable by a user between the maximum first condition arm lateral cross-dimension 268 and the maximum second condition arm width 270 on a user-selected position of the second end 142 of the arm between the lowered position 190 and the raised position 192. For purpose of illustration and not limitation, the ratio of the dimensions of the maximum second condition arm width 270 to the maximum second condition arm width 268 may be approximately between 1.33 to 1, 1.5 to 1, or 2 to 1, although other suitable ratios can be used.

Figure 9D:
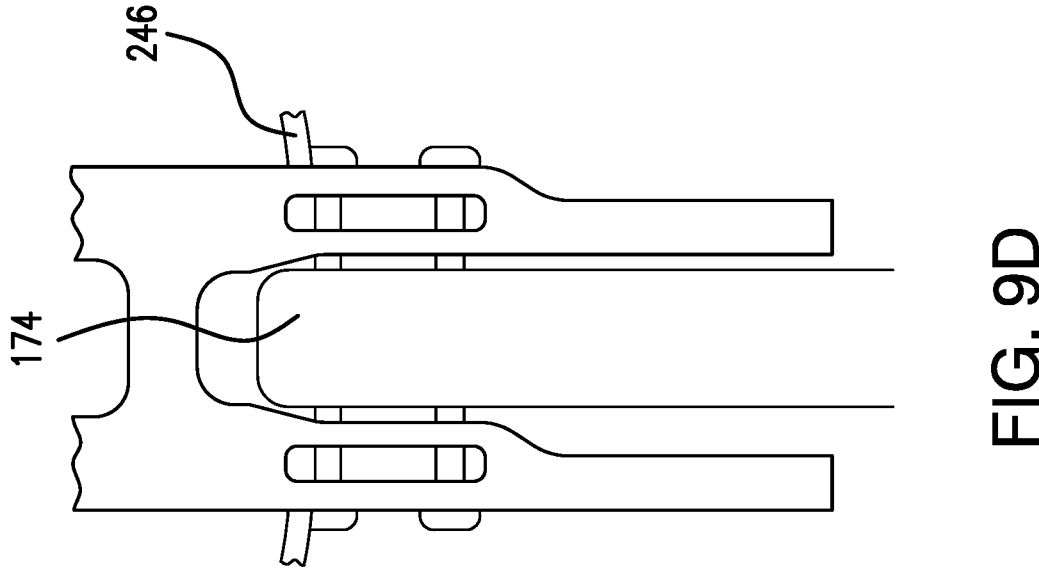
FIG. 9D is a plan view of an alternative embodiment of the arm and leg of FIG. 9B having a wire frame with a fixed coupling at the leg.
Figure 9C:
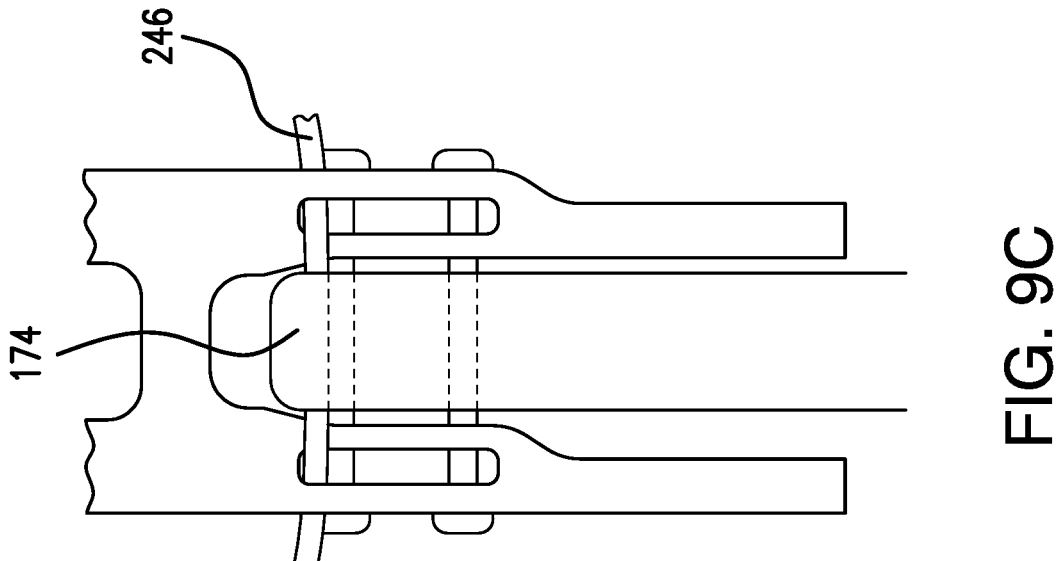
FIG. 9C is a plan view of an embodiment of the arm and leg of FIG. 9B having a wire frame with a slidable coupling through the leg.

As shown in FIG. 9C, the wire frame 246 can be coupled to the end of the leg 174. The coupling between the wire frame 246 and the end of the leg 174 can be of any suitable type. For example, the sliding can be a slidable coupling (as shown in FIG. 9C) or a fixed coupling (as shown in FIG. 9D).

Figure 13:
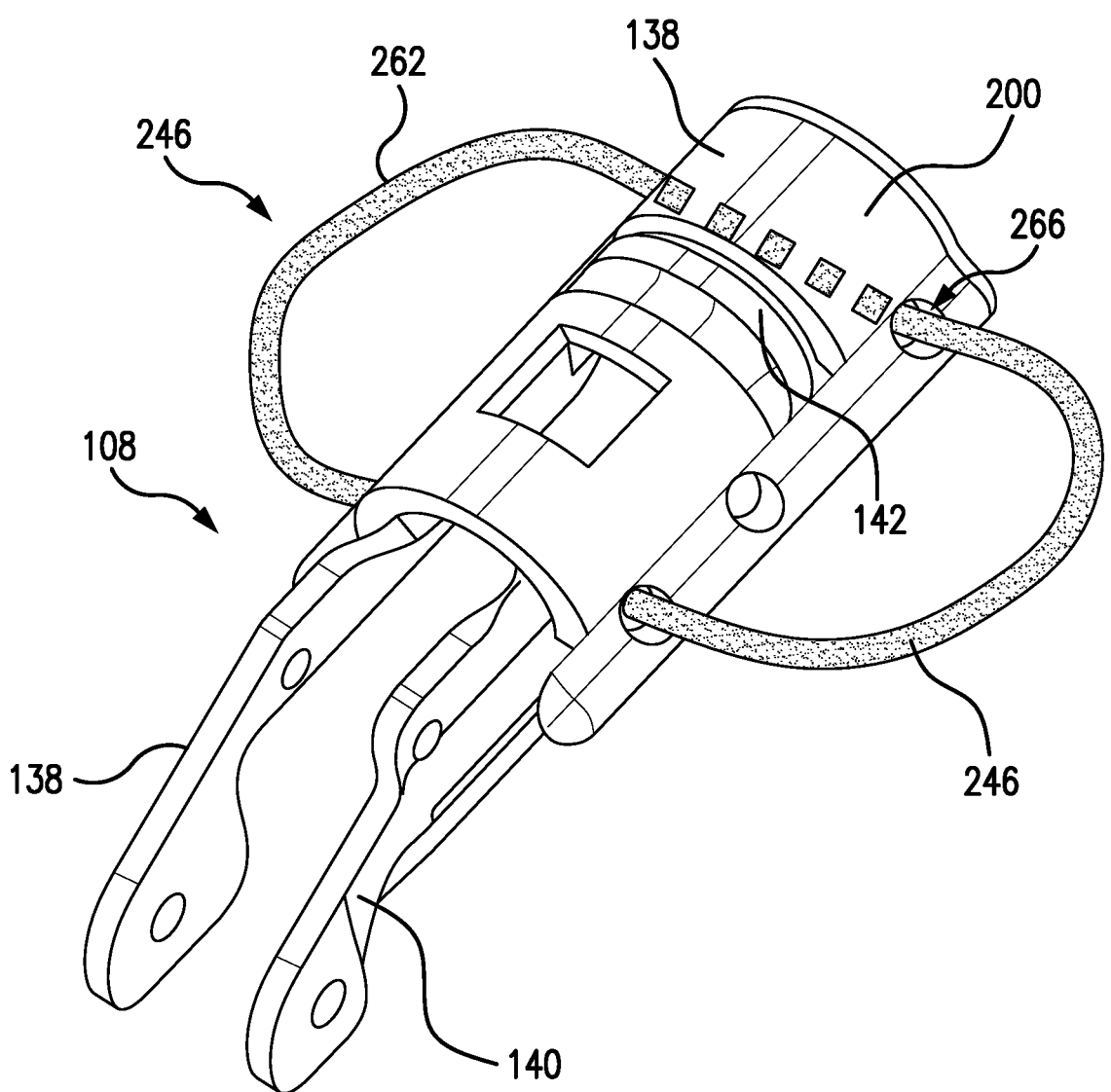
FIG. 13 is a perspective view of an embodiment of an arm having a size adaptor attached thereto and a slidingly engaged wire frame.

In accordance with an additional aspect of the subject disclosed herein, and shown in FIG. 13, the body portion 138 can further include a size adapter 200. Further, the interconnection portion 266 can be slidingly engaged with the size adapter 200 of the body portion 138. The size adapter 200 may be a separate component connected to body portion 138, such as by molding the size adapter 200 to body portion 138 or connecting size adapter to body portion 138 via a snap-fit connection or a fastener, such as one or more rivets, for example. Size adapter 200 may alternatively be integrally formed with body portion 138 so as to form a monolithic structure which may be achieved through additive manufacturing or the like. Size adapter 200 can extend longitudinally beyond the second end 142 of the body portion 138. Likewise, the interconnection portion 266 can extend beyond the length of the second end 142 of the body portion 138. The tunable wire frame 246 can function in conjunction with the size adapter 200 in a similar manner as in prior embodiments disclosed herein. That is, when the fixation device 104 is confined on one side by the heart anatomy upon delivery, the wire frame 246 can tune itself via the slidable engagement with the size adapter 200 attachment. For example, if the fixation device 104 is confined by the location of a heart wall against the first wire segment 262, the first wire segment 262 can deform upon force applied by the heart wall. This deformation of the first wire segment 262 can cause the interconnection portion 266 to slide relative to the body portion 138 and the size adapter 200 towards the side of the second wire segment 264, thus reducing the width of the first wire segment 262 and extending the width of the wire segment on the opposing side. Alternatively, depending on the position of the heart anatomy, the second wire segment 264 can similarly be reduced in width, such that the first wire segment 262 can be extended in width. The increase arm width on one side and decreased width on the other side can cause the corresponding contact patch area of the leaflets to be maintained. For purpose of illustration and not limitation, the overall width of the tunable wire frame 246 may be approximately 1.33, 1.5, or 2 times the width of size adaptor 200, although other suitable widths can be used.

For the embodiments illustrated herein, the wire frame 246 can have any suitable shape or structure, including a single piece structure, round wire, or non-round wire. The wire frame 246 can be formed of any suitable material, including Nitinol, or a sheet or strip of elastic material.

For the embodiments illustrated herein, the maximum first condition arm lateral cross-dimension 268 can be less than an inner diameter of an interventional catheter configured to deliver the tunable fixation device 104. The maximum second condition arm width 170 can be greater than the inner diameter of the interventional catheter.

As previously noted, and in accordance with the disclosed subject matter, the fixation device 104 further includes at least one gripping element 116, for example, the first gripping element 116 and second gripping element 118 as shown in FIG. 1. The gripping element 116 can be moveable relative to the at least one arm 108 to capture a native leaflet therebetween. In particular, the at least one gripping element 116 has a first end 228 coupled to a portion of the fixation device and a second end 230 moveable relative to the at least one arm 108. In accordance with the disclosed subject matter, each arm can be configured to define or have a trough 145. The trough can be configured to receive the gripping element 116 therein.

As embodied herein, each gripping element includes a plurality of friction elements 152, such as in rows. For example, each gripping element 116, 118 can have at least four rows of friction elements 152. The friction elements 152 can allow for improved tissue engagement during leaflet capture. If the fixation device requires adjustment after an initial leaflet capture, the arms can be opened, the gripping element can be raised vertically, and tissue can disengage from the fixation device, facilitating re-grasp and capture.

For example, and with reference again to FIG. 1, and as further embodied herein, each gripping element 116, 118 can be biased toward each respective arm 108, 110. Prior to leaflet capture, each gripping element 116, 118 can be moved inwardly toward a longitudinal center of the device (i.e., away from each respective arm 108, 110) and held with the aid of one or more gripping element lines (not shown) which can be in the form of sutures, wires, rods, cables, polymeric lines, or other suitable structures. The gripping line elements can be operatively connected with the gripping elements 116, 118 in a variety of ways, such as by being threaded through loops (not shown) disposed on the gripping elements 116, 118.

For each embodiment disclosed herein, the fixation device can further include an assembly to move the arms between various defined positions, for example, and not limitation, and with reference to FIG. 1, the fixation device embodied herein includes two link members or legs 168, each leg 168 having a first end which is rotatably joined with one of the arms 108, 110 and a second end which is rotatably joined with a base 170. The base 170 can be operatively connected with a stud 176 which can be operatively attached to a distal end of a delivery shaft (not shown for clarity). In some embodiments, the stud 176 can be threaded so that the distal end of a delivery shaft can attach to the stud 176 by a screw-type action. Further, the connection point between the stud 176 and the distal end of a delivery shaft can be disposed within the coupling member 174. However, the distal end of a delivery shaft and stud 176 can be operatively connected by any mechanism which is releasable to allow the fixation device 104 to be detached. The stud can be axially extendable and retractable to move the base and therefore the legs 168 which rotate the arms 108, 110 between closed, open and inverted positions. Likewise, immobilization of the stud, such as by a locking mechanism 178, can hold the legs 168 in place and therefore lock the arms 108, 110 in a desired position. Further details are disclosed in the patents and publications incorporated by reference herein.

The embodiments illustrated herein are adapted for repair of a heart valve, such as a mitral valve, using an antegrade approach from a patient's left atrium. Prior to a procedure, imaging and various tests can be performed to anticipate and diagnose a patient's individual circumstances and assist a physician in selecting a fixation device with components, such as the size adapter 200, having the desired parameters. Indeed, a physician can select a desired fixation device from a plurality of fixation devices having varied parameters and features. Further, after imaging a patient, a physician can configure a selected fixation device with desired components, such as a desired size adapter 200. Alternatively, various components, such as the size adapter 200 can be attached to the at least one arm during the manufacturing process. A manufacturing advantage of including a size adapter 200 is that the same body portion 138 can be manufactured and an optional size adapter can be manufactured separately. Additionally or alternatively, pre-shaping of wire frame 246 geometries may be made available in anticipation of different anatomic placement positions in the valve.

Figure 14:
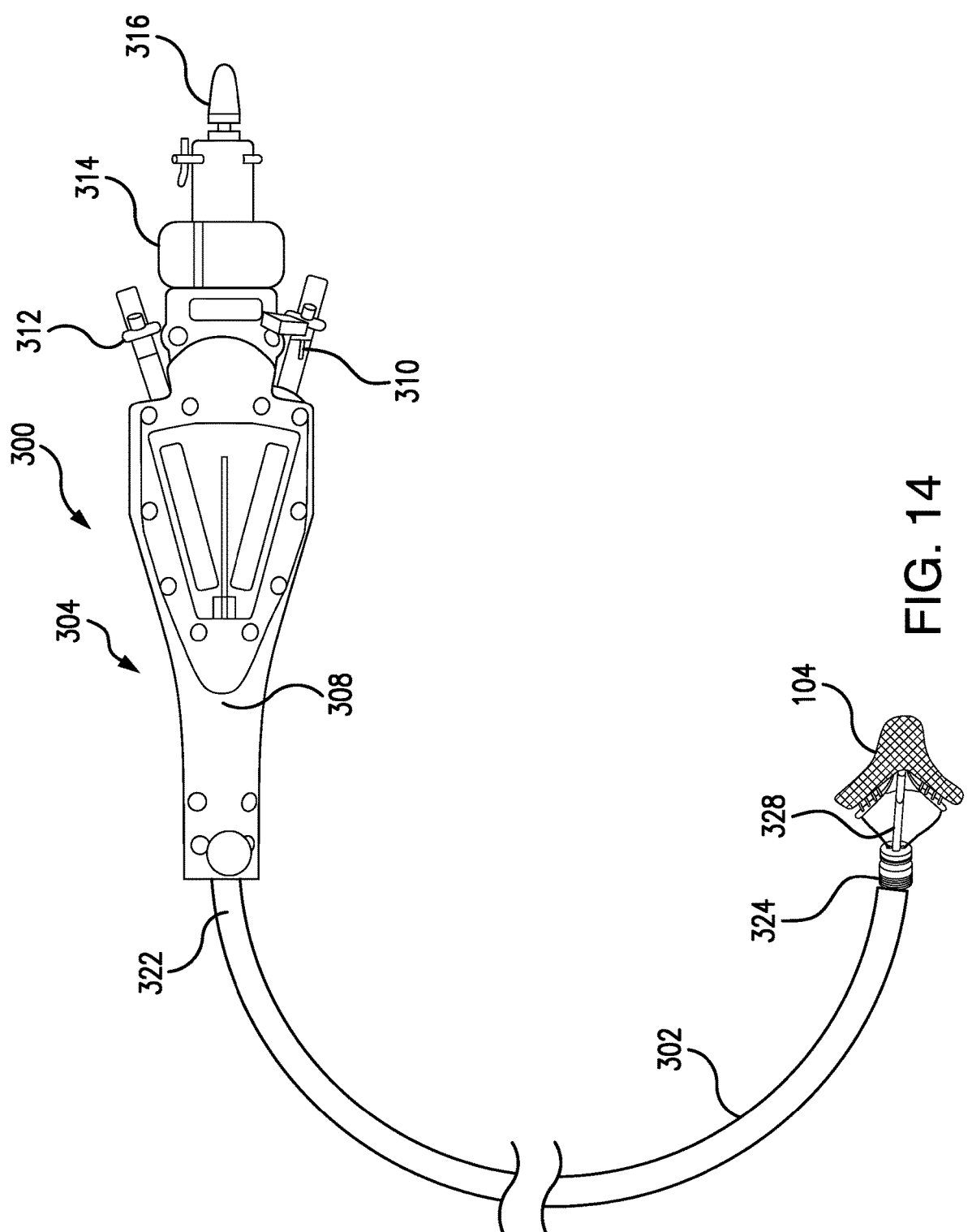
FIG. 14 is a top view of an interventional catheter assembly in accordance with the disclosed subject matter.

Referring to FIG. 14, for purpose of illustration and not limitation, an exemplary interventional catheter assembly 300 is provided for delivery of the fixation device 104. That is, the interventional catheter assembly 300 can be used to introduce and position fixation device 104. The interventional catheter assembly 200 can include an interventional catheter 302, having a proximal end portion 322 and a distal end portion 324, and a handle 304 attached to the proximal end portion 322. Fixation device 104 can be removably coupleable to the distal end portion 324 for delivery to a site within the body, for example, the mitral valve or the tricuspid valve. Extending from the distal end portion 324 is actuator rod 328. The actuator rod 328 is connectable with the fixation device 104 and can act to manipulate the fixation device 104, for example, opening and closing the arms. Handle 304 of the interventional catheter assembly 300 is shown, including main body 308, gripping element line handle 312, lock line handle 310, actuator rod control 314, and actuator rod handle 316, among other features.

During a procedure, to access a valve, such as a mitral valve or a tricuspid valve, the interventional catheter 302 can be inserted from a puncture in the femoral vein, through the inferior vena cava and into the right atrium. For access to the mitral valve, the interventional catheter 302 can extend through a puncture in a fossa of the interatrial septum and curve so that the distal end portion 324 is directed over the mitral valve. For access to the tricuspid valve, the interventional catheter 302 can curve in the right atrium so that the distal end portion 324 is directed over the tricuspid valve. For any valve, the distal end portion 324 can be centered over an opening between the leaflets of the valve. The distal end portion 324 can be lowered into the valve, thereby lowering the fixation device into the ventricle. The distal end portion can be raised and lowered as desired for a procedure, such as a regurgitation correction procedure. Prior to a procedure, imaging and various tests can be performed to anticipate and diagnose a patient's individual circumstances and assist a physician in selecting a fixation device having the desired parameters.

While the embodiments disclosed herein utilize a push-to-open, pull-to-close mechanism for opening and closing arms it should be understood that other suitable mechanisms can be used, such as a pull-to-open, push-to-close mechanism. Likewise, other actuation elements can be used for deployment of the gripping elements.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A tunable fixation device for fixation of leaflets of a heart valve comprising:

a central assembly;

at least one arm moveably coupled to the central assembly to be moveable between a closed position and an open position, the at least one arm comprising a body portion having a first end and a second end and a longitudinal axis defined therebetween and a transverse axis perpendicular to the longitudinal axis, the at least one arm further comprising a wire frame coupled to the body portion, the wire frame having a first wire segment, a second wire segment, and an interconnection portion interconnecting the first wire segment to the second wire segment, the interconnection portion slidingly engaged with the body portion, wherein the first wire segment is configured to deform upon force applied to the second wire segment by sliding movement of the interconnection portion relative to the body portion, and the second wire segment is configured to deform upon force applied to the first wire segment by sliding movement of the interconnection portion relative to the body portion; and at least one gripping element moveable relative to the at least one arm to capture a native leaflet therebetween.

2. The fixation device of claim 1, wherein the wire frame is fixed at a location along a length of the body portion.

3. The fixation device of claim 2, wherein the wire frame has a maximum first condition arm lateral cross-dimension with the wire frame in a first condition, and the wire frame has a maximum second condition arm width with the wire frame in a second condition, wherein the maximum second condition arm width is greater than the maximum first condition arm lateral cross-dimension.

4. The fixation device of claim 3, wherein the wire frame is configured to:

slide longitudinally outwardly through the second end of the body portion towards the first condition and decrease in width and elongate in length, and slide longitudinally inwardly through the second end of the body portion towards the second condition and increase in width and decrease in length.

5. The fixation device of claim 4, wherein the wire frame is biased towards the second condition and configured to move towards the first condition when the first wire segment is pushed transversely inwardly from an external force.

6. The fixation device of claim 1, wherein the body portion has at least one coupling slot configured to couple the at least one arm to a leg, wherein an end of the leg slides longitudinally within the at least one coupling slot.

7. The fixation device of claim 6, wherein the end of the leg is tunable between a lowered position and raised position.

8. The fixation device of claim 7, wherein the wire frame is coupled to the end of the leg.

9. The fixation device of claim 8, wherein when the end of the leg is in a raised position, the wire frame has a maximum second condition arm width.

10. The fixation device of claim 9, wherein when the end of the leg is in a lowered position, the wire frame has a maximum first condition arm lateral cross-dimension.

11. The fixation device of claim 10, wherein the maximum second condition arm width is greater than the maximum first condition arm lateral cross-dimension.

12. The fixation device of claim 11, wherein the width of the wire frame is tunable by a user between the maximum first condition arm lateral cross-dimension and the maximum second condition arm width on a user-selected position of the second end of the arm between the lowered position and the raised position.

13. The fixation device of claim 8, wherein the coupling between the wire frame and the end of the leg is a slidable coupling.

14. The fixation device of claim 8, wherein the coupling between the wire frame and the end of the leg is a fixed coupling.

15. The fixation device of claim 1, the body portion includes a size adapter and the interconnection portion is slidingly engaged with the size adapter of the body portion.

16. The fixation device of claim 15, wherein the size adapter extends longitudinally beyond the second end of the body portion.

17. The fixation device of claim 15, wherein the interconnection portion extends beyond the length of the second end of the body portion.

18. The fixation device of claim 1, wherein the first wire segment and second wire segment are secured to opposite sides of the body portion and extend laterally outwardly to form respective first and second loops.

19. The fixation device of claim 18, wherein the first and second wire segments are configured to deform such that decreasing the size of the first loop increases the size of the second loop, and decreasing the size of the second loop increases the size of the first loop.

20. The fixation device of claim 1, wherein the first wire segment defines a first lateral extent of the tunable fixation device, and the second wire segment defines a second lateral extent of the fixation device, and wherein deforming the first wire segment positions the first lateral extent closer to the longitudinal axis than the second lateral extent, and deforming the second wire segment positions the second lateral extent closer to the longitudinal axis than the first lateral extent.

\* \* \* \* \*